United States Patent [19]
Sorensen

[11] Patent Number: 5,255,187
[45] Date of Patent: Oct. 19, 1993

[54] COMPUTER AIDED MEDICAL DIAGNOSTIC METHOD AND APPARATUS

[76] Inventor: Mark C. Sorensen, 11 N. Second St., Apt. 502, Philadelphia, Pa. 19106

[21] Appl. No.: 503,879

[22] Filed: Apr. 3, 1990

[51] Int. Cl.$^5$ ............................................. G06F 15/00
[52] U.S. Cl. ..................... 364/413.02; 382/6; 345/117
[58] Field of Search ............... 340/715; 364/413.02, 364/413.01; 382/6

[56] References Cited

U.S. PATENT DOCUMENTS

| | | | |
|---|---|---|---|
| 4,290,114 | 9/1981 | Sinay | 364/900 |
| 4,338,811 | 7/1982 | Miyagi et al. | 364/498 |
| 4,625,278 | 11/1986 | Wong | 364/413.02 |
| 4,642,780 | 2/1987 | Thomson | 364/512 |
| 4,648,028 | 3/1987 | DeKlotz et al. | 364/188 |
| 4,733,354 | 3/1988 | Potter et al. | 364/415 |
| 4,849,885 | 7/1989 | Stillwagon et al. | 364/413.1 |
| 4,945,478 | 7/1990 | Merickel et al. | 364/413.22 |
| 4,974,598 | 12/1990 | John | 128/700 |
| 5,079,698 | 1/1992 | Grenier et al. | 364/413.13 |

OTHER PUBLICATIONS

Document entitled "Software 'Doctor' Prescribes Remedies" *IEEE Spectrum Magazine*, pp. 43–48, Oct., 1986.
Document entitled "An Overview of Methods For Computer-Assisted Medical Decision Making", Reggia, James A. and Tuhrim, Stanley, pp. 3–45.
Document entitled "Computer-Based Consultation: Electrolyte and Acid-Base Disorders", Bleich, Howard L., *The American Journal of Medicine*, pp. 285–291 (1972).
Document entitled "Computerized Triage of Pediatric Patients: Automated Triage Algorithms", Wilson, Linda Ornelas and Wilson, Frank P., *Ann Emerg Med*, Dec., 1981.
Document entitled "Production Rules as a Representation For a Knowledge-Based Consultation Program", Davis, Randall and Buchanan, G., *Artificial Intelligence*, pp. 98–130 (1977).
Document entitled "A Production Rule System For Neurological Localization", Reggia, James A. *IEEE*, pp. 254–260, Reprinted from *Proceedings of the Second Annual Symposium on Computer Applications in Medical Care*, (1978).
Document entitled "Internist-I, An Experimental Computer-Based Diagnostic Consultant For General Internal Medicine", Miller, Randolph A., Pople, Harry E., Jr., *The New England Journal of Medicine*, pp. 468–475, Aug. (1982).
Document entitled "Pattern-Based Interactive Diagnosis of Multiple Disorders: The MEDAS System", Ben-Bassat, Moshe, Carlson, Richard W., Puri, Venod K., *IEEE*, Reprinted from *IEEE Transactions on Pattern Analysis and Machine Intelligence*, pp. 223–250, Mar., 1980.
Document entitled "Computer-Aided Diagnosis of Acute Abdominal Pain", deDombal, F. T., Leaper, D. J., Staniland, J. R., *British Medical Journal*, pp. 9–13, Apr. (1972).
Document entitled "A Mathematical Approach to Medical Diagnosis: Application to Congenital Heart Disease", Warner, Homer R., Toronto Alan F., Veasey, George L. Reprinted from *Journal of the American Medical Assoc.*, pp. 144–158, vol. 177, Jul. (1961).
Brochure entitled "BRS/Saunders Colleague", Sep., 1984.
Article entitled "Ask*Med: A New Approach to Information For Medical Practitioners", Bernstein, L. M., Williamson, R. E., Korman, L. Y., *IEEE*, p. 336, (1985).

(List continued on next page.)

Primary Examiner—Roy N. Envall, Jr.
Assistant Examiner—Laura Brutman
Attorney, Agent, or Firm—Woodcock Washburn Kurtz Mackiewicz & Norris

[57] ABSTRACT

An interactive computerized apparatus and method for presenting medical information for diagnosis and study of disease is disclosed. Findings of disease are color-coded according the significance of the presence or absence of each finding in ruling in or ruling out the possibility of the disease being present and presented on a color display to aid a physician or other user to diagnose or study disease.

31 Claims, 18 Drawing Sheets

OTHER PUBLICATIONS

Document entitled "Explanation Capabilities For Medical Consultation Systems" (Tutorial), Shortliffe, Edward H., Departments of Medicine and Computer Science, Stanford University, Stanford, Calif., p. 193.

Document entitled "Explaining and Justifying Expert Consulting Programs", Swartout, William R., *Proceedings of the Seventh Int'l Joint Conference on Artificial Intelligence*, pp. 254-271, (1981).

Article entitled "Charles Meader and His Differential Diagnosis Machine", McDonald, Clement J., *Medcomp*.

Brochure entitled "$N^2$ PDB—The Physician's Data Base Manager", $N^2$ *Squared Computing*.

Brochure entitled "$N^2$ Microcomputer Medical Software Programs for Computer-Aided Diagnostic Decision-Support", $N^2$ *Squared Computing*.

Article entitled "Construction & Use of Knowledge Couplers & Networks & a POMR on a Personal Computer", Weed, Lawrence L., Hertzberg, Richard Y. and Wood, Christopher, *IEEE*, (1985).

Article entitled "The Use and Construction of Problem-Knowledge Couplers, The Knowledge Coupler Editor", Weed, L. L., Hertzberg, R. Y., *IEEE*, pp. 831-836, (1983).

Document entitled "Preliminary Evaluations of Reconsider, A Diagnostic Prompting Program", Yamashita, Dale T., Erlbaum, Mark S., Harrison, Peter B., *Medical Information Science*, University of California, pp. 92-96.

Document entitled "DXplain An Evolving Diagnostic Decision-Support System", Barnett, Octo G., Cimino, James J., Hupp, Jon A., *JAMA*, pp. 67-74, Jul., (1987).

Document entitled "Quick (Quick Index to Caduceus Knowledge): Using the Internist-1/Caduceus Knowledge Base As an Electronic Textbook of Medicine", First, Michael B., Soffer, Lynn J., Miller, Randolph A., *Computers and Biomedical Research 18*, pp. 137-165, (1985).

Article entitled "An Electronic Textbook of Medicine", Masarie, F. E., Jr., Miller, R. A., First, M. B. *IEEE*, p. 335 University of Pittsburgh School of Medicine, (1985).

Document entitled "The Internist-1/Quick Medical Reference Project—Status Report", Miller, Randolph A., McNeil, Melissa A., Challinor, Sue M., *The Western Journal of Medicine*, pp. 816-822, Dec., (1986).

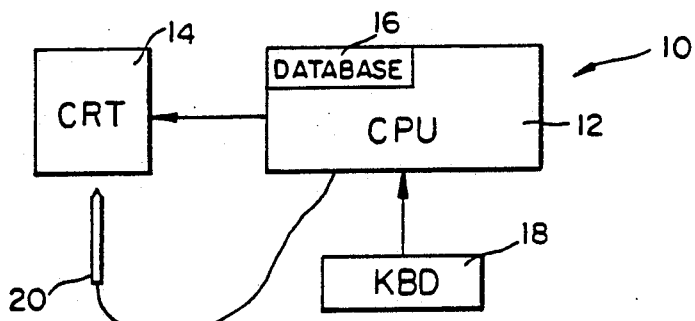

First line:

H = history findings        V = vital signs
P = physical findings       G = general appearance
L = lab findings            H = head and neck findings
X = x-ray findings          N = neurologic findings
S = special studies         E = extremity findings
                            O = back findings
                            C = chest findings
                            A = abdominal findings
                            P = pelvic findings
                            R = rectal findings Second line:

P = purple findings
O = orange findings
Yu = yellow findings which usually occur
G = green findings
Y = remaining yellow findings Third line:

L = life and or organ threatening emergencies
V = very common diseases
C = common diseases
O = diseases which occur occasionally
R = rare diseases

FIG. 2

FIG. 3 from 68

72

> For each presented finding, designated by the physician as being present or absent, the computer simultaneously designates all other findings as present or absent, which were predetermined to be:
>
> 1. some /= presented finding
>    (elevated WBC is some /= leukocytosis)
>
> 2. automatically present or absent, given the presence or absence of the presented finding (if "male" is present then "female" is automatically absent)

74

> On the basis of the presence or absence of its findings, each disease is assigned to one of the following categories by the computer:
>
> 1. Likely possibilities, or diseases which must be assumed to be present until proven otherwise
>
> 2. Other possibilities
>
> 3. Unlikely possibilities
>
> 4. Diseases eliminated from consideration
>
> This is done on the bases of a fairly simple set of rules, easily learned and memorized by the physician (see Addendum 5). Knowing the rules, the physician may quickly and easily modify or override the computer's decisions (see below)

to 76

FIG. 8 from 60

84 — Using a display employing both text and graphics, (see Addenda 6,7) the physician may access the following additional information, in order to rule in or rule out each disease possibility:

1. The finding represented by each color bar

2. Additional findings, whose availability is indicated by the colored dots below each column of colored bars 3. Additional information about any of the above findings The physician may also:

1. Identify, and temporarily eliminate, non-specific findings, in order to simplify the diagnostic process 2. Assign one or more diseases to another category (see page 5), or temporarily eliminate them from the display and therefore from consideration 86 — The physician may, at any time:

1. Move on to the next set of diseases (up to 5) within the same category to 59 ← 2. Select a smaller and/or different group of diseases 3. Select one disease, for consideration, for which the findings present are diagnostic, or which he considers the most likely possibility → to 26

4. Go back and continue working through the findings for all the diseases initially generated, and not yet eliminated → to 62

FIG. 10

TUBAL PREGNANCY

PURPLE FINDINGS

|   | Male |
|---|---|
|   | − B-HCG |
|   | p. Hysterectomy |
| R | p. Menopause |
| R | Pre-menarchal |

GREEN FINDINGS

| P | + | B-HCG |
|---|---|---|
|   | + | Ultrasound/Laproscopy |

ORANGE FINDINGS, and
YELLOW FINDINGS which usually occur

| P | Female |
|---|---|
| P | + B-HCG |
|   | Pelvic pain |
|   | Change from usual menstrual pattern |
|   | Adnexal tenderness, unilateral |
|   | Adnexal mass |
|   | 20- 30 years old |

FIG. 14

TUBAL PREGNANCY

YELLOW FINDINGS, other

>     Predisposing factors
>         IUD
>         p. Hx: Tubal pregnancy
>                PID
>                Endometriosis
>         Infertility
>     + Culdocentesis
>     Bulging of cul de sac
>     Rectal tenesmus
> BR  Elevated WBC (<20,000)
> BR  Decreased HCT

FIG. 15

TUBAL PREGNANCY

Tubal pregnancy is the implantation of a conceptus in the fallopian tube instead of the uterus. As a result of enlargement and trophoblastic activity, the conceptus is aborted from the tube or the tube ruptures (8-12 weeks after implantation). Tubal rupture often leads to massive intraabdominal hemorrhage

|Disease #1|2nd Disease|Next Disease|4th Disease|Last Disease|
|---|---|---|---|---|
| | | | |☐|
| | | | |☐|
| |☐ π| | |☐|
| | |☐ π| |☐ π|
|☐ π|☐ *| |☐ *|☐ *|
|☐ *| |☐ *|Ⓖ ☐|Ⓖ ☐|

|Disease #1|2nd Disease|Next Disease|4th Disease|Last Disease|
|---|---|---|---|---|
|O|O| |Yu|Yu|
|O| | |Yu| |
|Yu| | | | |
|Yu| | | | |
|Yu| | | | |

\* Right Lower Quadrant Pain  
π Nausea and/or vomiting

|Y=3|Y=2|Y=4|Y=4|Y=1|
|---|---|---|---|---|
|P G Y|P Y Yu|Y|G Y|Y|

FIG. 17

| Disease #1 | 2nd Disease | Next Disease | 4th Disease | Last Disease |
|---|---|---|---|---|

(column layout figure)

| O | O |  | Yu | Yu |
| O |  |  | Yu |  |
| Yu |  |  |  |  |
| Yu |  |  |  |  |
| Yu |  |  |  |  |

Disease #1
PURPLE FINDING
— Laparotomy
GREEN FINDING
+ Laparotomy
YELLOW FINDINGS
G  Abdominal  x-ray
Br Diarrhea
Br UA WBC's/RBC's (few)
Br Testicular pain
Br Constipation
    RLQ skin hypesthesia
Br Dysuria RLQ: sentinel loop
     fecalith – Right lower quadrant pain
– Nausea and/or vomiting

| Y=3 | Y=2 | Y=4 | Y=4 | Y=1 |
| P\|G\|Y | P\|Y\|Yu | Y | G\|Y | Y |

FIG. 18

| Disease #1 | 2nd Disease | Next Disease | 4th Disease | Last Disease |
|---|---|---|---|---|

(table structure represents diagram layout)

ç  Change from menstrual periods
ϖ  +B-HCG
§  Unilateral adnexal mass

-Right lower quadrant pain
-Nausea and/or vomiting

** Constipation

2nd Disease
PURPLE FINDING
-Ultrasound

| Y=10 | Y=2 | Y=4 | Y=4 | Y=2 |
|---|---|---|---|---|
| P G Y | P Y Yu | Y | G Y | Y |

FIG. 19

| Disease #1 | Next Disease | 4th Disease | Last Disease |
|---|---|---|---|

⑥ § ⑥

| O |  | Yu | Yu |
|---|---|---|---|
| O |  | Yu |  |
| Yu |  | § Lab test XYZ | F⊕ |
| Yu |  |  |  |
| Yu |  |  |  |

—Right lower quadrant
—Nausea and/or vomiting

Lab test XYZ
The results of this test depend on a large number of variables... There are many false positive and false negative results including... therefore the results should be interpreted with caution...

| Y=10 | Y=4 | Y=4 | Y=2 |
|---|---|---|---|
| P G | Y | G Y | Y |

FIG. 20

COMPUTER AIDED MEDICAL DIAGNOSTIC METHOD AND APPARATUS

FIELD OF THE INVENTION

The present invention relates generally to the area of computer aided medical diagnosis. More particularly, the present invention is directed to a computer aided method and apparatus employing color to quickly convey diagnostic information to a physician or other medical personnel.

BACKGROUND OF THE INVENTION

Quick and accurate diagnosis is crucial to many practices of medicine. In order for a physician (or other medical person) to quickly and accurately diagnose a condition, he must know not only all of the possible conditions or diseases associated with a particular finding or set of findings, but also which findings to look for in the patient.

Given a particular presentation such as chest pain, blurred vision, or cardiac arrhythmia, the physician needs to know:

1) which conditions and/or diseases to consider (i.e., what are the disease possibilities);

2) which manifestations or findings to look for; and 3) the significance of the presence or absence of each finding in ruling in or ruling out each condition and/or disease possibility.

Traditionally, this information has been obtained from experience or medical journals. While experience and the teachings of medical journals are invaluable, it is unrealistic to expect that a physician will be aware of every possibility associated with a set of findings, or that he will be aware of every finding that he should consider. It is also unrealistic to expect that a physician will have instant recall of everything that he has learned. Reliance upon textbooks and journals requires slow and methodical analysis, so they alone are not suitable for many practices of medicine.

One example of information that is useful for diagnosing a particular condition and/or disease is the frequency with which a particular finding occurs in patients suffering from a particular condition and/or disease under consideration. Another example of useful information is the specificity, or "evoking strength" of the finding. The specificity answers the question: "Given a patient with this finding, how strongly should I (the physician) consider this diagnosis to be its explanation?"

In other words, while the frequency is an estimate of how often patients with the condition and/or disease exhibit the finding, the specificity is indicative of the frequency with which the finding manifests itself in patients not having the disease. Both the frequency and specificity of findings are extremely important, if not essential, to accurate diagnosis, but these are examples of information that no physician can always be expected to have at his fingertips.

The prior art generally contemplates the use of computer programs that apply symbolic reasoning, or "artificial intelligence", to assist the physician in making diagnoses in the field of general internal medicine. For example, see Randolph A. Miller, et al., *Internists: I, An Experimental Computer-Based Diagnostic Consultant For General Internal Medicine*, The New England Journal of Medicine, Vol. 307, Number 8, pp. 468-475 (August 1982). See also Michael B. First, et al., *QUICK (QUick) Index to Caduceus Knowledge; Using The Internists—I/-Caduceus Knowledge Base As An Electronic Textbook of Medicine*, Computers and Biomedical Research, Vol. 18, pp. 137-165 (1985). And also, U.S. Pat. Nos. 4,290,114 (Sinay) and 4,733,354 (Potter, et al.). However, these systems are generally cumbersome to use and do not rapidly and efficiently convey diagnostic information to the physician or other medical personnel. They therefore do not answer the need for a system that provides rapid and accurate diagnostic information.

It is unlikely that any machine, including a programmed computer, will ever replace the skill and intuition of a human physician in rendering a medical diagnosis. However, available resources should be employed to the maximum extent possible to aid physician in rendering quick and accurate diagnoses. These resources should be employed in such a way that they complement, rather than replace, the physician in diagnosing a patient's condition Thus, an object of the present invention to is provide a computer aided method of presenting diagnostic information to a physician or other medical personnel in such a manner that conditions and/or diseases can be quickly and accurately diagnosed.

A further object of the invention is to provide a computer aided, bedside diagnostic assistance system.

Still a further object of the present invention is to provide a computer aided study program for use by a physician or other medical personnel in studying a wide range of diseases and afflictions.

SUMMARY OF THE INVENTION

The invention provides an interactive computerized apparatus and method for presenting medical information for diagnosis and study of disease. The interactive computerized apparatus of the invention comprises processing means for processing data indicative of disease findings, including assigning color codes to the disease findings; a database containing data indicative of diseases and findings; input means for entering data indicative of at lease one disease or finding to the processing means; and output means for providing a color display of diseases and findings, the diseases and findings being color coded and categorized on the display according to a set of rules.

In the preferred embodiment, the processing means is a computer, the color display is a color CRT or a color LCD display, and the input means is a keyboard or a light pen.

The use of color, in association with a computer, as described herein, has several distinct advantages over present methods of communicating diagnostic information, using either conventional textbooks and journals or computers. The use of color in the present invention permits quick and clear communication of the aspect of diagnostic information which is the most difficult to learn and remember—the significance of the presence or absence of findings in ruling in or ruling out associated disease possibilities. The color-coded symbols make it much easier for physicians to learn and remember diagnostic information. Using the apparatus and method of the invention, it is possible for a physician to quickly and accurately recall and apply a large amount of diagnostic information, literally at the bedside. It is possible for a physician to work through a large number of disease possibilities quickly and efficiently, and yet also thoroughly and systematically. Colors guide the physician or other user through the diagnostic process, almost without his even having to think about one of the most difficult and error producing aspects of that process, i.e. knowing the significance of the presence or absence of the findings he is searching for. The present invention, however, serves primarily as a supplier of information to physicians, rather than as a substitute for the physician's thinking, judgement, and intuition, since it is unrealistic to believe that a computer can replace the physician.

The apparatus and method of the invention communicate to the physician the reasons for the few diagnostic decisions made for him, i.e., why a group of diseases are considered likely possibilities for diagnosis. The physician is then able to quickly, easily and intelligently modify or override the computer's decisions and thus maintain complete control over every step of the diagnostic process. This is a great advantage over other computerized diagnostic assistance programs which have recently been developed, and which do replace, to a large extent, physician thinking.

BRIEF DESCRIPTION OF THE DRAWINGS

FIG. 1 shows a diagrammatic representation of an apparatus suitable for practicing the invention.

FIG. 2 shows diagrammatic representation of a matrix used to determine the preferable order of presentation of findings for a set of diseases.

Figure 3:
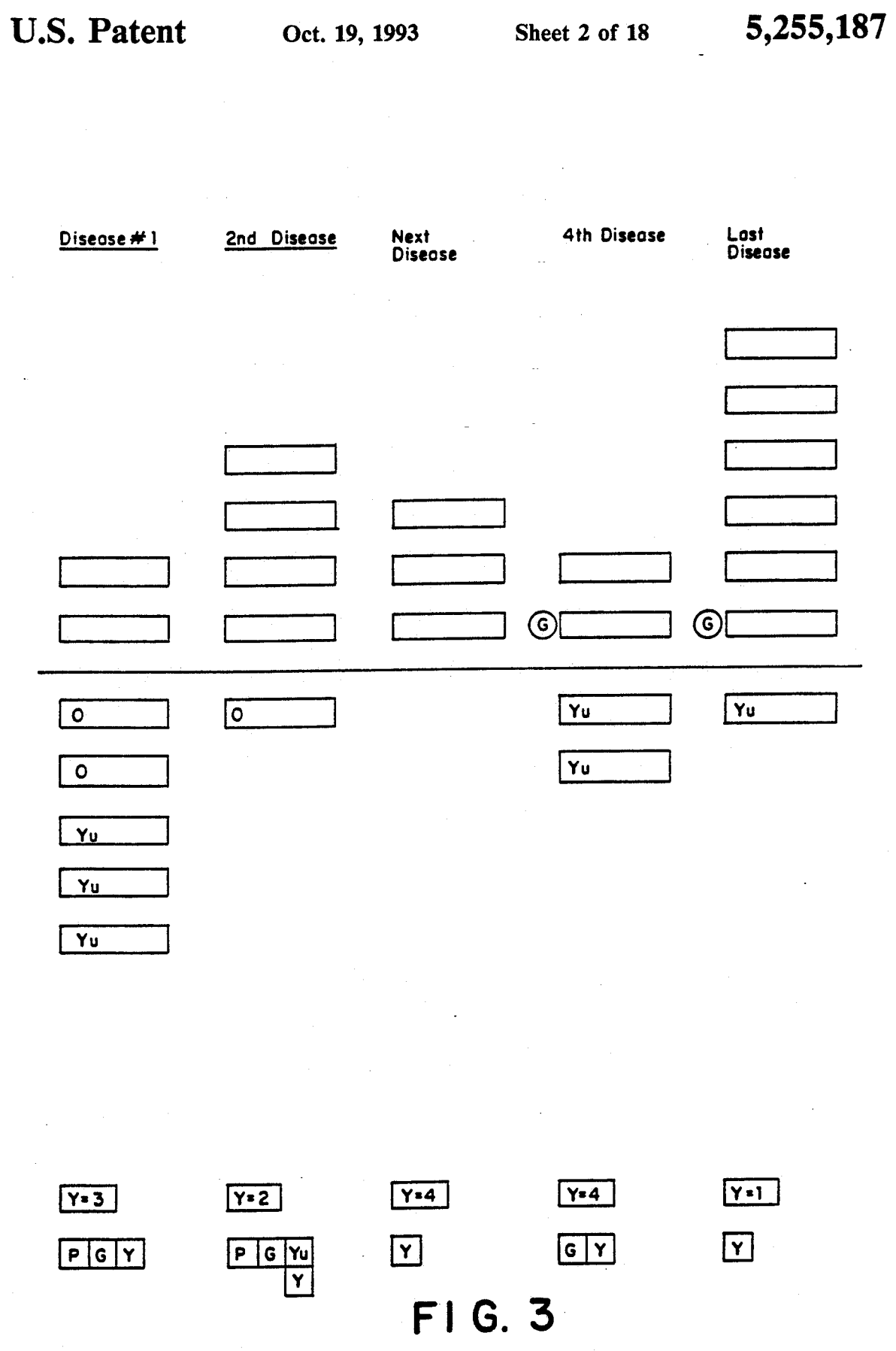

FIG. 3 shows a diagrammatic representation of a visual display of a group of diseases.

FIGS. 4-13 show a flow chart of the operation of the bedside diagnostic assistance program and the study program.

FIG. 14 shows a diagrammatic representation of a visual display of the findings of the disease tubal pregnancy color-coded according to the invention.

FIG. 15 is a continuation of the diagrammatic representation of a visual display of the findings of the disease tubal pregnancy color-coded according to the invention shown in FIG. 14.

FIG. 16 shows a diagrammatic representation of a visual display in the study program.

FIGS. 17-20 show a diagrammatic representations of visual displays in the bedside diagnostic assistance program.

DETAILED DESCRIPTION OF THE INVENTION

Figure 4:
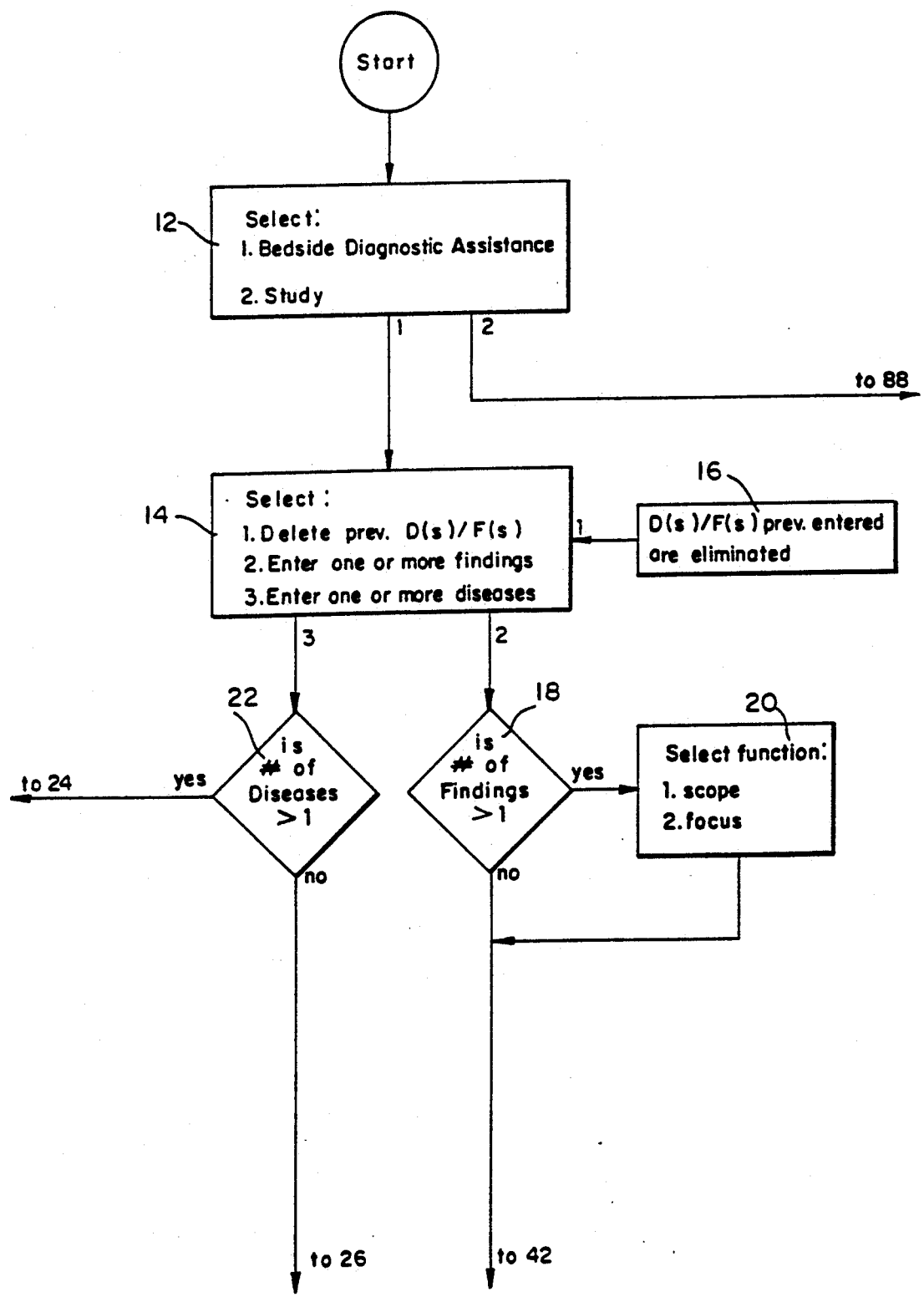

Findings as used herein include disease manifestations, or other factors, the presence or absence of which may be used to help rule in or rule out associated disease possibilities. Disease manifestations are conditions which are caused by an associated disease. They include symptoms (which are looked for by taking a history from the patient), signs (which are looked for by physically examining the patient), or other conditions which are looked for by performing laboratory tests, taking X-rays, or doing other studies. Factors are conditions which are not caused by an associated disease, but whose presence or absence, make that disease more or less likely to be present in a patient. Factors include the patient's age, sex, race, and/or other predisposing conditions. For example, a manifestation of tubal pregnancy is lower abdominal or pelvic pain. Factors which make tubal pregnancy more or less likely are the patient's sex and age and a past history of pelvic infection or surgery. Diseases are defined herein as conditions for which physicians are generally called upon to render diagnosis or treatment.

Referring now to the drawings, wherein like numerals represent like elements, there is illustrated in FIG. 1 an apparatus 10 for practicing the present invention. The apparatus 10 comprises a processing means 12, which in the preferred embodiment is a desktop computer such as an IBM PC or a portable computer such as a Zenith laptop computer (hereinafter the term "computer" will be employed to refer to the processing means 12, but it should be understood that adoption of such a term is not intended to be limiting in any respect.) The function of the computer 12 is to process data indicative of diseases and/or findings entered into the computer (by input means described hereinafter), including assigning color codes to the diseases and/or findings and categorizing the same, both according to a prescribed set of rules to be described. Data such as disease and/or finding selection is entered into the computer 12 via an input means which may comprise either a keyboard 18, a light pen 20, or both. Output means displays the color coded diseases and/or findings, and the categorizations of the same, as determined by the processing means. The output means may comprise a color CRT 14, a color LCD display, or any other color display device. A computer program operates as below described to apply the prescribed set of rules to input data to yield the color coded, categorized display of findings and/or diseases.

A database is stored in a memory 16 associated with the computer 16. The database contains data indicative of a plurality of diseases and findings, as will become evident hereinafter.

Findings of diseases are programmed in well-known manner into the computer according to the function or significance of the presence or absence of each finding in ruling in or ruling out the possibility of the associated disease being present in a patient and are assigned a color for each disease. Thus a finding such as bleeding may be coded color A in one disease and color B in another disease. Findings for a disease may be obtained by consulting standard medical texts, physicians or other sources.

Each finding is assigned a primary color according to the following rules:

| PRIMARY COLOR | FUNCTION OR SIGNIFICANCE |
|---|---|
| First | First color findings, if present, definitely rule out associated diseases. First color finding are never present with associated diseases. |
| Second | Second color findings, if absent, definitely rule out, or help to rule out associated diseases. Second color finding are always present, or almost always present with associated diseases. Second color findings, if present, support the diagnosis. Second color findings are more or less specific for associated diseases. |
| Third | Third color findings, if present, support the diagnosis. Third color findings are generally specific for, but not diagnostic for a given disease. |
| Fourth | Fourth color findings, if present, are diagnostic for associated diseases. Fourth color findings are absolutely specific for associated diseases. |

Findings diagnostic for a disease are characteristic of or indicate the presence of a particular disease. Findings specific for a disease have a real and fixed relationship to the disease and usually constitute a characteristic of the disease.

In one embodiment of the invention, the first color is purple; the second color is orange, the third color is yellow, the fourth color is green.

There is often more than one fourth color finding per disease. All fourth color findings must be present for these findings to be diagnostic for a disease. There are often many (more than twenty) third color findings per disease. Therefore, in order to increase the usefulness of these findings, they are divided into two groups: 1) those which usually occur with the associated disease, and 2) those which occur less frequently than that. Those third color findings which usually occur, are presented along with second color findings, both for study and for bedside diagnostic assistance. Their absence is less helpful than the absence of orange findings in ruling out diseases.

As the physician works through the diagnostic program, first eliminating certain diseases and then eventually identifying the disease which is present in the patient, the colored findings help him to do the following:

First color findings, if present, eliminate diseases which, even though they are known to cause a particular presentation, do not need to be considered. Second color findings, if absent, definitely rule out diseases or help to rule out diseases. Third color findings which usually occur, if absent, also help to rule out diseases, though less so than second color findings. Second color findings, and third color findings which usually occur, if present, may identify one or more likely disease possibilities. The other, remaining third color findings, if absent, aid little in diagnosis. If present, however, they may identify other likely possibilities, or they may help determine which of several likely possibilities is the most likely. Fourth color findings, if present, are diagnostic for whichever disease is associated with it or them.

The findings of a disease are further assigned secondary colors according to a set of rules. The secondary colors are presented as color-coded symbols, preferably dots, next to the color-coded symbol or name of the finding (which appears in the primary color). The secondary colors also indicate the function or significance of the presence or absence of the findings associated with them, in ruling in or ruling out the diseases associated with the findings. More than one secondary color may be assigned to a finding. The secondary colors are assigned to findings according to the following rules:

(i) a first secondary color is assigned to second primary color findings and fourth primary color findings if these findings are always present with associated diseases, and the opposite of said second primary color and fourth primary color findings are then presented as first primary color findings. (If these findings are absent, or if the opposites of these findings are present, the associated diseases are definitely ruled out or eliminated.)

(ii) a second secondary color is assigned to fourth primary color findings if these findings are almost always present with associated diseases and said fourth primary color findings are also presented as second primary color findings.

(iii) a third secondary color is assigned to fourth primary color findings if these findings usually occur with associated diseases and said fourth primary color findings are also presented as third primary color findings. (These findings are presented as third primary color findings along with other third primary color findings which usually occur with associated diseases.)

(iv) a fourth secondary color is assigned to second and third primary color findings if each of these findings is, by itself, very specific, though not diagnostic for its associated disease. (These findings, if present, help identify diseases which are likely possibilities.)

(iv) a fourth secondary color is assigned to a fourth primary color finding if said finding is alone very specific, though not diagnostic for its associated disease. (These findings, if present, also help identify likely disease possibilities.)

(v) a fifth secondary color is assigned to second, third, and fourth primary color findings if each of these findings is often the only finding present with its associated disease. (The presence of each of these findings identifies diseases which must be presumed to be present until proven otherwise, even if it is the only finding present with a given patient.)

(vi) a sixth secondary color is assigned to third primary color findings if these findings are consistent with their associated diseases but occur much more frequently with other diseases. (This color emphasizes to the physician that the finding is consistent with the associated disease, and may prevent him from erroneously diverting his attention to another disease with which the finding is more often associated. That is, it prevents the associated finding from being a red herring.)

(vii) more than one secondary color may be assigned to a primary color finding.

(viii) red is assigned as a secondary color to a first or fourth primary color finding if the finding should be used with caution in ruling in or ruling out an associated disease.

The first four secondary colors are preferably the same color as the four primary colors, respectively. This is because these secondary colors convey much the same meaning, or in some cases, exactly the same meaning as the respective primary colors. Thus, in the preferred embodiment of the invention, the first secondary color is purple, the second secondary color is orange, the third secondary color is yellow and the fourth secondary color is green. In the preferred embodiment of the invention the fifth secondary color is blue and the sixth secondary color is brown.

Diseases are also color-coded according to the following rule: red is assigned to a disease which is a life or organ threatening emergency. (This color alerts the physician to diseases which must be assumed to be present until proven otherwise, even if there is relatively little evidence to support the diagnosis.)

It may be necessary, or useful to assign additional colors to findings or diseases in order to:

1) identify the function or significance of the presence or absence of a particular finding or set of findings in ruling in or ruling out associated disease possibilities, or 2) identify a particular set of diseases as being more or less of a threat, in one way or another, to life and/or well being of human beings or other living species, as compared to other diseases, and which therefore require more or less prompt or extensive diagnostic consideration than other diseases.

The apparatus of the invention is capable of operation in one of two primary methods or routines, one for bedside diagnosis of disease, the other for study of disease. When the findings are presented for the purpose of studying diseases, the findings for each disease are grouped into colored sets, each finding in a set having the same primary color. These sets are then presented, sequentially, for each disease, one disease at a time.

When the findings are presented for bedside diagnostic assistance, that is, for working through a (sometimes large) group of disease possibilities, the findings are also grouped into colored sets. In this case, however, each colored set contains all the findings, for all the diseases in the group, each with the same primary color. For example, the first color findings for each disease are grouped together and presented first. Then all the second color findings for each disease are grouped together and presented next. Grouping and displaying of like color findings is repeated for each color.

To assist the physician in diagnosing a disease as quickly as possible, it is preferable that the color-coded findings be presented in a predetermined order. The predetermined order of presentation of findings may be changed by the physician if he wishes the findings to appear in a different order.

The findings are preferably presented in the following order:

1. First primary color findings (usually 0-3 per disease). These findings eliminate diseases which, even though they are known to cause the patients presentation, do not need to be considered.
2. Second primary color findings (usually 0-3 per disease). These findings eliminate, or help to rule out diseases. They may also identify one or more likely possibilities.
3. Third primary color findings which usually occur (usually 1-5 per disease). These findings help rule out other diseases and also identify likely possibilities.
4. Fourth color findings (usually 0-3 per disease). These are diagnostic for the disease. However, determining the presence or absence of fourth color findings is often risky or expensive in terms of time or resources. Therefore, the additional third color findings (often there are more than 20 per disease) may be used to determine which of several likely possibilities is most likely, before using the fourth color findings for that disease.

Within each set of findings, it is preferable to present findings in the following order: history findings, physical findings, lab findings, x-ray findings, special studies. Working first through history findings prepares the physician's mind to search for physical findings. The presence or absence of these two sets of findings ca usually be determined fairly quickly and easily before moving on to the other sets of findings, the presence or absence of which is increasingly difficult, time consuming, expensive or risky to determine.

Also, it is preferable to present physical findings in the following order: vital signs, general appearance, head and neck findings, neurologic findings, extremity findings, back findings, chest findings, abdominal findings, pelvic findings, rectal findings in order to allow the physician to search for these findings in a systematic, efficient way.

Finally, it is preferable to present the findings for diseases in the following order: life and/or organ threatening emergencies (L), very common diseases (V), common diseases (C), diseases which occur occasionally (0), rare diseases (0). Life and/or organ threatening emergencies should be considered first. It is more efficient to consider first, those diseases which, a priori, are most likely to be the cause of the patient's illness, before considering diseases which are less likely to be the cause.

Considering all of the above, the computer uses the matrix show in FIG. 2 to determine the preferable order of presentation of findings for a set of diseases. As shown in FIG. 2, to determine the order of presentation of the findings, the computer moves down the matrix before moving across, and moves across : before moving across ::. The computer presents for a group of diseases first, history, first primary color findings for L,V,C,O,R diseases; then history, second primary color findings for L,V,C,O,R diseases; then history, third primary color findings which usually occur for L,V,C O,R diseases, then physical, first primary color findings for L,V,C,O,R diseases and so on down the matrix, and finally, special study, remaining third color findings for L,V,C,O,R diseases are presented.

While working through the bedside diagnostic program (while considering a group of disease possibilities), the physician indicates which findings are present, absent, or cannot be determined for those diseases. The physician determines the presence or absence of each finding by taking a history from the patient, by physically examining the patient, or by having lab tests, X-rays, or other studies performed. After the physician has indicated which findings are present, absent or undetermined, the computer assigns each of the above diseases to a group or category of diseases based upon the likelihood of the disease being present in the patient. In a preferred embodiment of the invention, the computer assigns disease possibilities to four different categories according to the following rules:

Category 1 (Category E)

Diseases eliminated from consideration, even though they are known to cause the patient's presentation are assigned to category 1. Diseases are assigned to this category if first primary color findings are present, or if associated findings with a first secondary color are absent.

Category 2 (Category L)

Diseases that are likely possibilities, or diseases which must be assumed to be present until proven otherwise, even if there is relatively little evidence to support the diagnosis are assigned to category 2. Diseases are assigned to this category if: (a) all associated fourth color findings are present, (b) any associated finding with the fourth color as a secondary color is present, (c) three or more findings other than first color findings are present and no second color color findings are absent, (d) four or more findings are present, and not more than one second color finding is absent, other than second color findings having the first secondary color associated therewith, (e) five or more findings are present, and not more than two second color findings are absent, (f) one or more fifth color findings are present, or, (g) two or more findings are present for a life or organ threatening emergency.

Category 3 (Category U)

Diseases that are unlikely possibilities are assigned to category 3. Diseases are assigned to this category if more than two second color findings are absent, other than second color findings having a first secondary color associated therewith; or if two or more findings are absent which have a second secondary color associated therewith.

Category 4 (Category O)

Diseases that are other possibilities are assigned to category 4. All diseases that are not assigned to categories 1-3 are assigned to this category.

After diseases have been grouped into the above categories, the computer presents the results of the above diagnostic process for each group of diseases, using a display employing both text and symbols. An example of a preferred display is shown in FIG. 3. In this example, the first, second, third, and fourth primary colors of findings are purple, orange, yellow and green, respectively, The fourth secondary color of findings is green. As shown in FIG. 3, the names of the diseases are presented across the top of the display. The names of the first two diseases, which appear in bold type and which are underlined, are the names of life and/or organ threatening emergencies. According to the invention, these names would actually appear in red. The other diseases are not life and/or organ threatening emergencies, and their names would therefore appear in black or white.

The screen shows for each disease a column of bars beneath the name of the disease, which represent findings for that disease which have been determined to be present or absent by the physician. The bars above the line represent findings which are present and which therefore support the diagnosis for each associated disease. The bars below the line represent findings which are absent and which are therefore evidence against the diagnosis for each disease.

In this example, the bars above the line represent orange findings, yellow findings which usually occur, and other yellow findings. The bars above the line are not color-coded because the frequency with which these findings occur for each disease is no longer important in ruling in or ruling out that disease. The importance of orange and yellow findings which are present is their specificity for an associated disease, not the frequency with which they occur with that disease. The specificity of these findings for each disease is indicated using the fourth secondary color which in this example is green. This secondary color is assigned to the above findings which are very specific (but not diagnostic) for the associated disease. In FIG. 3, these secondary color assignments are represented by a dot, labeled with a "G", next to the bar which represents the finding. According to the preferred embodiment of the invention, these symbols would actually appear as unlabeled green dots.

In this example, the bars below the line represent orange findings, and yellow findings which usually occur with each disease. In FIG. 3, the above primary colors of these findings are indicated by labelling the bars with an "O" for orange findings, and a "Yu" for yellow findings which usually occur. According to the preferred embodiment of the invention, the above symbols would actually appear as unlabeled orange and yellow bars respectively. The assignment of green to these findings, as a secondary color, is not shown in the display, because the specificity of these absent findings for each disease is not important.

Along the bottom of the display, additional boxes (squares or rectangles) are displayed for each disease. These boxes are color-coded according to the primary color code and indicate additional findings associated with each disease. The first row of boxes represent yellow findings, other than those which usually occur with each disease, which have been determined by the physician to be absent. The number in each box indicates the number of findings represented by that box. Each of these yellow findings is not represented by a bar (unlike yellow findings which usually occur) because the absence of each of these yellow findings alone is of almost no help in ruling out its associated disease. However, the absence of a group of these findings is somewhat helpful, and is therefore indicated using the above symbol. According to the preferred embodiment of the invention, these symbols would actually appear as yellow boxes. "Y=" would not appear in these boxes. Only the number would appear. The second row of boxes represent findings which have already been presented to the physician, but whose presence or absence could not be determined at the time, or findings which have not yet been presented. These boxes prompt the physician to look for additional specific findings in order to rule in or rule out each disease. In FIG. 3, the boxes labeled with "P", "G", "Yu" and "Y" represent purple findings, green findings, yellow findings which usually occur, and other yellow findings, respectively. In the preferred embodiment of the invention, the above first, second and fourth symbols would actually appear as unlabeled purple, green and yellow boxes, respectively. The third symbol would appear as a yellow box, labeled with a "u".

Knowing the meaning of the colors of the names of the diseases, and the meaning of the colors and positions of the bars, and the rules used by the computer to assign diseases to various categories of likelihood, the physician can see, almost at a glance, why each disease in this example was assigned to the category of likely possibilities, or diseases which must be assumed to be present until proven otherwise.

Disease #1 must be assumed to be present until proven otherwise because it is a life and/or organ threatening emergency and two of its findings are present in the patient. The name of the disease would be shown in red and two finding blocks are shown above the line.

The 2nd Disease is assigned to this category for two reasons. It must be assumed to be present until proven otherwise because it is a life and/or organ threatening emergency and more than two of its findings are present in the patient. The name of the disease is shown in red and four findings are shown above the line. It is also considered a likely possibility because four of its findings are present and only one orange finding is absent.

The Next Disease is considered a likely possibility because three findings are present and no orange findings are absent.

The 4th Disease is considered a likely possibility because a finding which is considered very specific for this disease (a finding with green as a secondary color) is present in the patient.

The Last Disease is considered a likely possibility for two reasons. More than three findings are present and no orange findings are absent. Also, a finding is present which is very specific for this disease. This finding is shown above the line with green as a secondary color next to it.

As will be seen later, the above display can be used by the physician to access additional diagnostic information in order to further rule in or rule out each disease possibility. It also enables physicians to very quickly, easily, and intelligently, modify or override the only diagnostic decision which the computer has made for them, the assignment of diseases to the above categories.

Consider now the bedside diagnostic assistance program during operation FIGS. 4-10 illustrate the program operation. Beginning with FIG. 4, with the portable apparatus 10 in hand, or at his side, the physician initiates patient diagnosis by selecting at block 12 between the bedside diagnostic assistance program and the study program. The study program will be described in greater detail in relation to FIG. 11. For the moment, assume the physician has chosen the bedside diagnostic assistance program. At block 14, the physician next determines whether previously entered information will be deleted or whether new information will be entered. If the physician chooses to delete previously entered diseases or findings, such information is deleted at block 16 after appropriate identifying information has been provided.

If the physician chooses to enter one or more findings, or after information has been deleted, device 10 determines at 18 whether the number of findings is greater than one. If only one finding has been entered, device 10 proceeds to generate a list of diseases known to cause that finding, which will be described in greater detail in relation to FIG. 6. If the number of findings entered is greater than one, the physician must choose at block 20 between the scope or focus function in relation to each finding. If the physician chooses the scope function, device 10 generates a group of diseases, each of which causes one or more of the findings. If the physician chooses the focus function, device 10 generates a group of diseases, each of which causes all of the findings. After selecting between the scope and focus function, device 10 then generates a list of diseases known to cause the findings in question, which will be described in greater detail in relation to block 42 in FIG. 6.

If, at block 14, the physician choose to enter one or more diseases, device 10 determines at 22 whether the number of diseases is greater than one. If only one disease has been entered, the physician makes a number of selections which are described in greater detail in relation to FIG. 5. If the number of diseases is determined at 22 to be greater than 1, device 10 proceeds to the program shown in FIG. 3, wherein it is determined at 24 whether the number of diseases is greater than 5.

Figure 5:
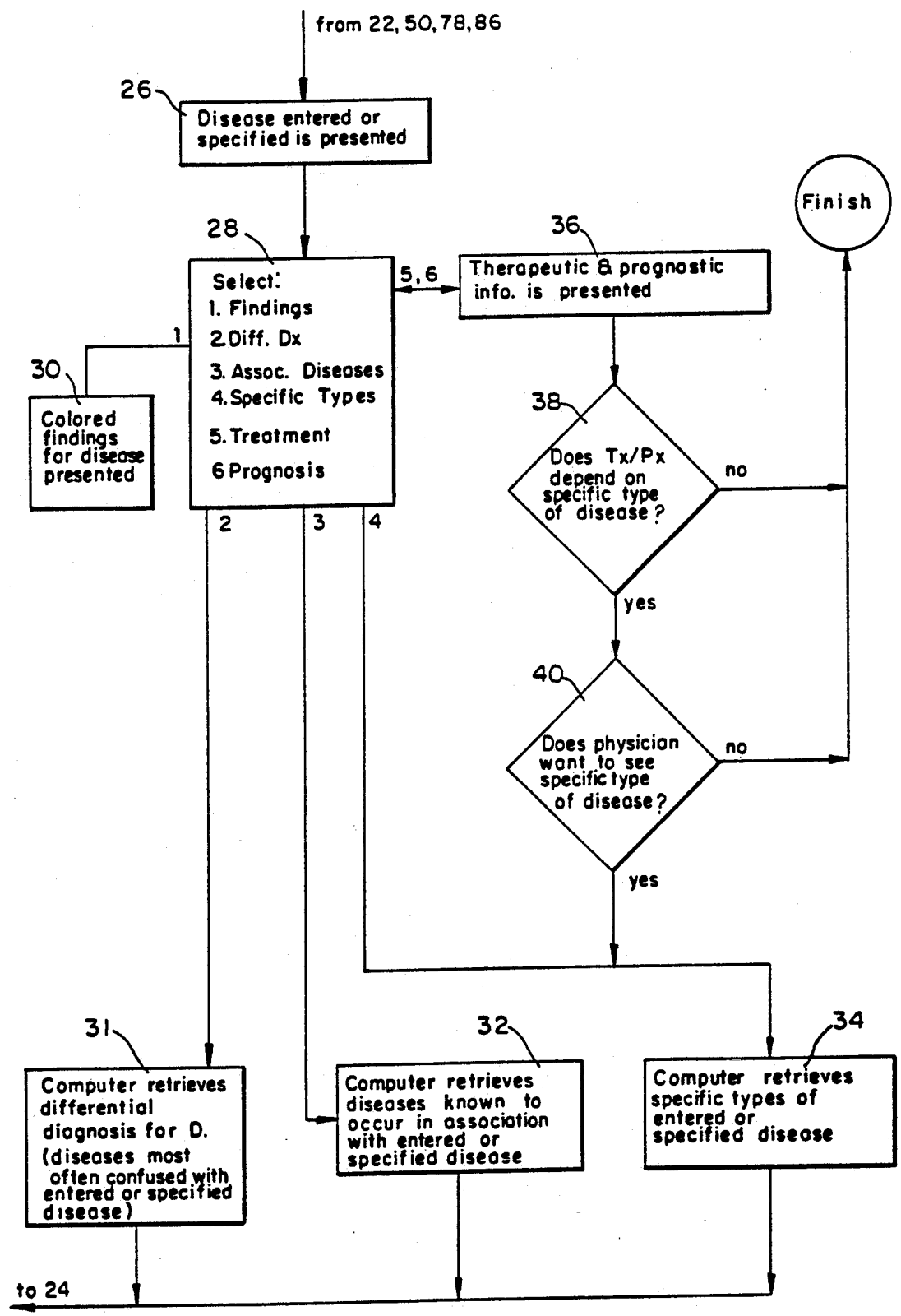

Referring now to FIG. 5, device 10 displays the disease entered in block 14 at block 26. Device 10 then proceeds to block 28 where the physician may choose to have device 10 display the findings, differential diagnosis, associated diseases, the specific types of diseases, treatment or prognosis of the disease entered in block 26. If at block 28 the physician selects the findings of the disease, the computer then proceeds to block 30 where device 10 presents the color coded findings for the disease.

Continuing with FIG. 5, if the physician wishes to know more about the differential diagnosis for the disease, device 10 then proceeds to block 31 where device lo retrieves the differential diagnosis for the entered disease. The differential diagnoses are the diseases most often confused with the entered disease. Device 10 then proceeds to block 24 which is described in greater detail in relation to FIG. 6. If at block 28 the physician wishes to know more about the associated diseases, device 10 will then proceed to block 32 where device 10 retrieves the diseases known to occur in association with the entered disease and then proceeds to block 24 which is described in greater relation to FIG. 6. If the physician wishes to know more about specific types of diseases, device 10 then proceeds to block 34 where device 10 retrieves the specific types of diseases and then proceeds to block 24 which is described in greater detail in relation to FIG. 6. If at block 28 the physician wishes to know more about the treatment and/or prognosis for the entered disease, device 10 then proceeds to block 36 where device 10 displays therapeutic and/or prognostic information about the entered disease. Device 10 then proceeds to 38 where device 10 determines whether or not the therapeutic and/or prognostic information depends on the specific type of disease. If the therapeutic and/or prognostic information does not depend on the specific type of disease, device 10 then finishes the bedside diagnostic assistance program. If the therapeutic and/or prognostic information does depend on the specific type of disease, device 10 then proceeds to 40 where device 10 determines whether the physician wants to see the specific types of disease. If the physician indicates that he does not wish to see the specific types of disease, device 10 finishes the bedside diagnostic program. If the physician indicates that he wishes to see the specific types of disease, device 10 then proceeds to block 34 where device 10 retrieves the specific types of the disease and then proceeds to block 24 which is described in greater detail in relation to FIG. 6.

Figure 6:
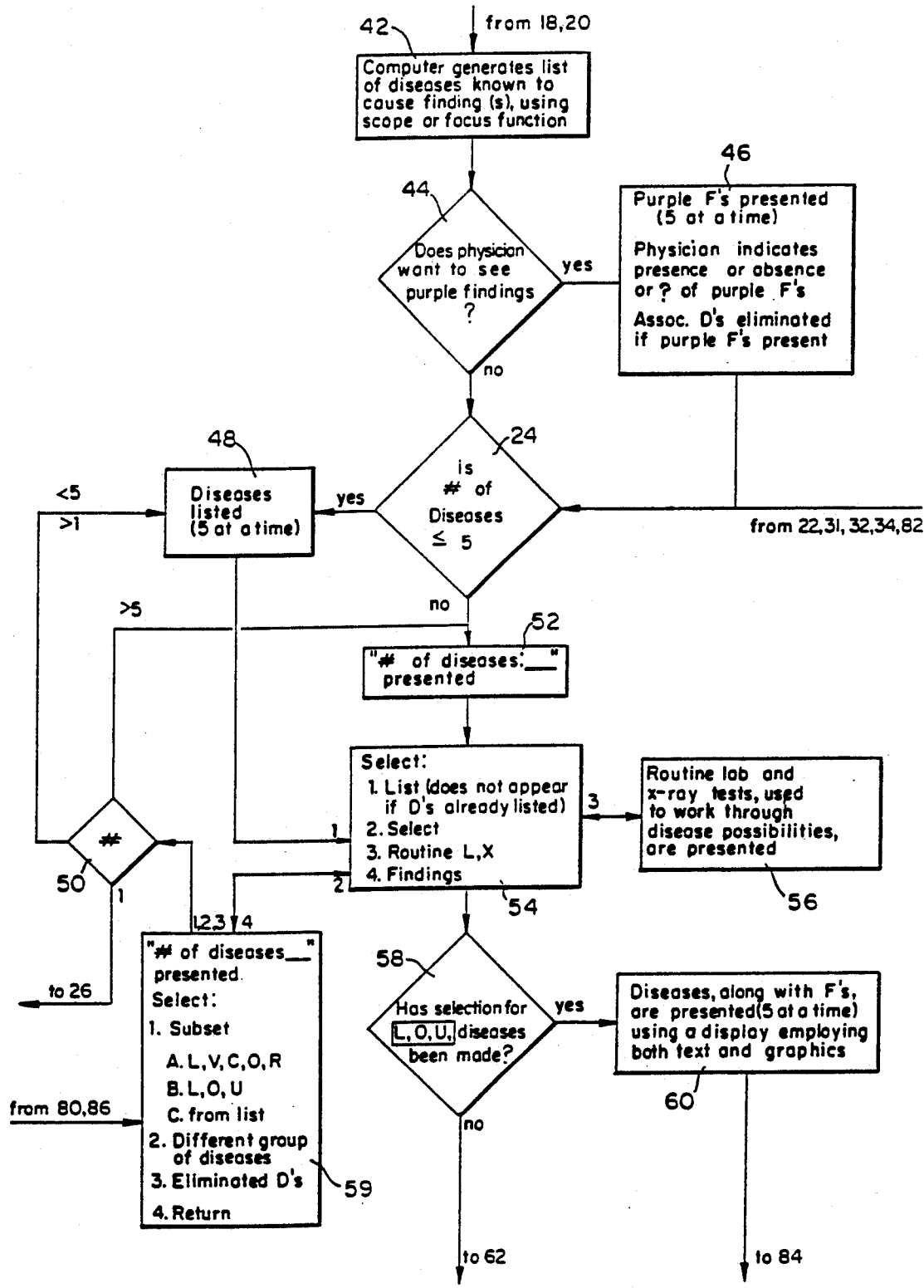

Referring now to FIG. 6, at block 42 device 10 generates a list of diseases known to cause the finding or findings (using the scope or focus function). Device 10 then proceeds to 44 where it is determined whether the physician wants to see the first primary color findings. If the physician indicates that he wishes to see the first primary color findings, device 10 proceeds to block 46 where the first primary color findings are presented 5 at a time. The physician indicates at block 46 the presence or absence of the first primary color findings in his patient, and device 10 eliminates diseases associated with each first primary color finding which is present. Device 10 then proceeds to block 24. At 44, if the physician indicates that he does not wish to see the first primary color findings, device 10 proceeds to block 24 where it is determined whether the number of diseases is less than or equal to 5. If the number of diseases is less than or equal to 5, device 10 proceeds to block 48 where the diseases are listed. If the number of diseases is greater than 5, device 10 proceeds to box 52 where device 10 presents the number of diseases. Device 10 then proceeds to box 5 where device 10 shows the physician a number of choices. The physician may have the diseases listed. (If the diseases have already been listed, this selection does not appear on the menu.) The physician may select a smaller and/or different group of diseases for consideration. He may access a list of the routine lab and X-ray studies which may be used to help rule in or rule out each disease possibility or he may access the colored findings for the diseases. If the physician chooses to list the diseases, device 10 proceeds to block 48, lists the diseases and returns to block 54.

If the physician chooses to select a smaller and/or different group of diseases for consideration, device 10 proceeds to block 59. He may then select (1) a subset of the diseases he is presently considering, (2) a different group of diseases, or (3) the diseases which have been eliminated from consideration using first primary color findings. He may also change his mind and decide not to select for a smaller or different group of diseases, in which case device 10 returns to block 54.

If the physician chooses to select a subset of diseases, he may do this in one of three ways. He may choose one or more of the following groups of diseases:

L=life and/or organ threatening emergencies
V=very common diseases
C=common diseases
O=occasional diseases
R=rare diseases V,C,O, and R refer to the frequency with which the diseases cause a particular finding or group of findings, or, if findings were not used to generate the diseases, the frequency with which the diseases occur, a priori, in the population in which the physician practices. Or the physician may select one or more of L,O, or U groups of diseases, or he may select one or more diseases from a list of diseases. The L,O,U groups of diseases are categorized by the likelihood of the disease being present in the patient based upon the findings known to present or absent at this point in the diagnostic routine.

If the physician chooses to select a different group of diseases, device 10 retrieves the finding or set of findings, or the disease or group of diseases used to generate the group of diseases which he is presently considering. Device 10 then presents the above finding or set of findings, or the name of the above disease or group of diseases, and returns to the menu at block 14, or block 28, or block 59. The physician may then use that menu to select a different group of diseases. For example, if, while considering a group of diseases named "differential diagnosis for appendicitis" a physician chooses to select a different group of diseases, device 10 retrieves and presents "appendicitis" (the name of the disease used to generate the above group) and returns to the menu at block 28. The physician may then use this menu to select for a different group of diseases, for example, diseases associated with appendicitis. If, while considering the group named "L,V,C causes of epigastric pain" he chooses to select a different group, device 10 retrieves the group of diseases used to generate the above group and presents the name of this group: "causes of gastric pain". Device 10 then returns to the menu at block 59. The physician may then use this menu to select a different subgroup of this group. If, instead, he chooses to select a still different group, device 10 retrieves and presents "epigastric pain", the finding used to generate the above group of diseases. Device 10 then returns to the menu at block 14. The physician may then use this menu to generate a different group of diseases.

If the physician chooses to see the diseases which were eliminated from consideration, i.e. category E diseases, device 10 retrieves and presents these diseases along with the first primary color findings used to eliminate them. The physician may then override device 10 decisions and return any of these diseases to the group of diseases he is presently considering. Device 10 then retrieves this latter group of diseases and returns to block 59.

After the physician has selected one or more diseases, device 10 proceeds to block 50 where device 10 determines the number of diseases selected. If just one disease was selected, device to proceeds to block 26 which is described in greater detail in relation to FIG. 5. If the number of diseases is greater than 1, but less than 5, device 10 proceeds to block 48. If the number of diseases is greater than 5, device 10 proceeds to block 52. If at block 54 the physician selects for routine lab and X-ray tests, device 10 proceeds to block 56 where a list of these tests is presented. The physician may then order these tests so that they can be performed while he is doing something else. If at block 54, the physician selects the findings for the diseases, device 10 then proceeds to block 58 where device 10 determines whether a selection for L,O,U diseases has been made. If a selection for L,O,U diseases has been made, device 10 then proceeds to box 60 where the diseases (5 at a time) along with the findings are presented using a display employing both text and graphics. Device 10 then proceeds to block 84, which is described in greater detail in relation to FIG. 10. If a selection for LOU diseases has not been made, device 10 then proceeds to block 62 which is described in greater detail in reference to FIG. 7.

Figure 7:
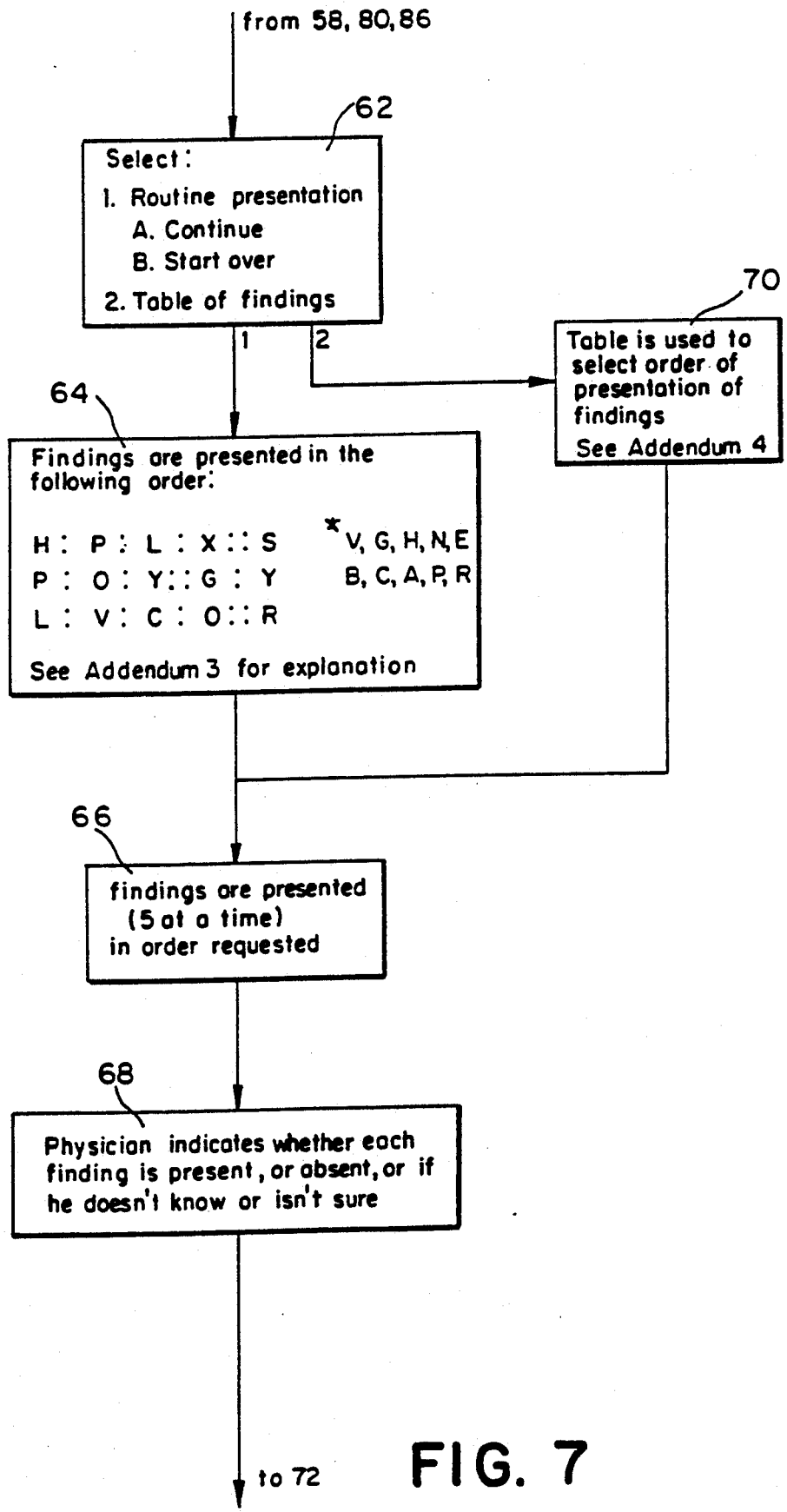

Referring now to FIG. 7, at block 62 the physician selects whether to have a routine presentation of the findings for the diseases or to choose a different order of presentation of the findings. If the physician selects a different order of presentation of the findings, device 10 proceeds to block 70 where device 10 presents a table for the physician to use to choose a different order of presentation of the findings. Device 10 then proceeds to block 66. If the physician chooses a routine presentation of the findings device 10 proceeds to block 64 where device 10 shows the physician in which order the findings will be presented. Device 10 then proceeds to block 66 where the findings are presented 5 at a time in the order requested. Device 10 then proceeds to block 68 where the physician indicates whether each finding is present or absent or if he does not know or is not sure whether the finding is present or absent. Device 10 then proceeds to block 72 which is described in greater detail in relation to FIG. 8.

Referring now to FIG. 8 at block 72, for each presented finding designated by the physician as being present or absent, device 10 simultaneously designates all other findings as present or absent which were determined to be (1) the same or equal to the presented finding, or (2) automatically present or absent given the presence or absence of the presented finding. Device 10 then proceeds to block 74 where device 10, on the basis of the presence or absence of the findings, each disease is assigned to one of the following categories by device 10.

Category 1—(L) Likely possibilities, or diseases which must be assumed to be presents until proven otherwise.
Category 2—(O) Other possibilities.
Category 3—(U) Unlikely possibilities.
Category 4—(E) Disease eliminated from consideration.

The first three of the categories are the L, O, or U groups of diseases which may be selected for at block 59. Device 10 then proceeds to block 76 which is described in greater detail in relation to FIG. 9.

Figure 9:
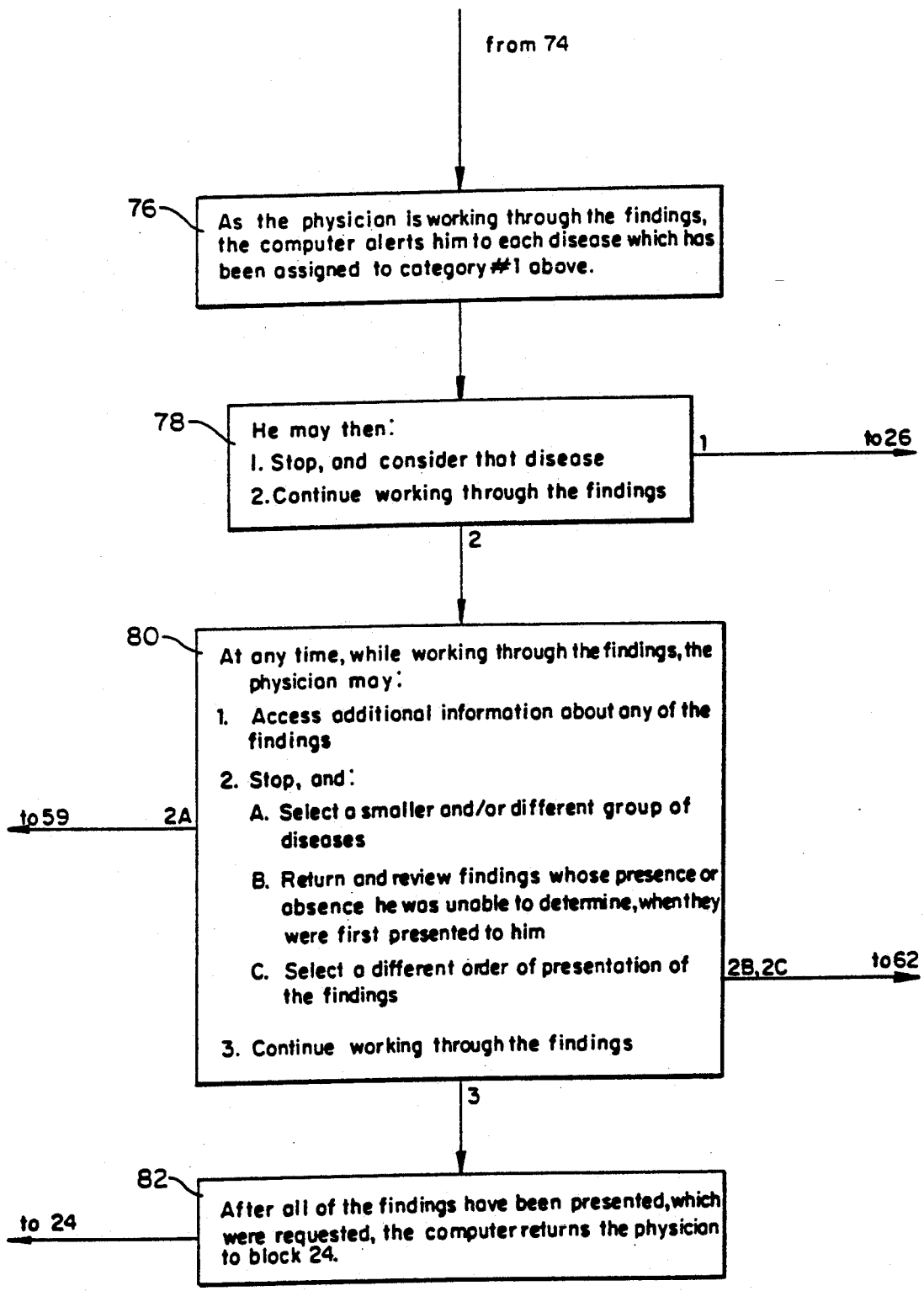

Referring now to FIG. 9, at block 76, device 10 alerts the physician to each disease which has been assigned to Category 1. Device 10 then proceeds to block 78 where the physician may stop and consider that disease or may continue working through the findings. If the physician chooses to stop and consider the disease, device 10 proceeds to block 26. If the physician selects to continue working through the findings, device 10 proceeds to block 80. At block 80 the physician may select to access additional information about any of the findings or the physician may stop and select a smaller and/or different group of diseases, return and review findings whose presence or absence he was unable to determine when they were first presented to him, or select a different order or presentation of the findings, or the physician may continue working through the findings. If the physician chooses to select a smaller or different group of diseases, device 10 proceeds to block 59. If the physician chooses to return and review findings whose presence or absence he was unable to determine when they were first presented to him, or the physician selects a different order of presentation of the findings, device 10 then proceeds to block 62. If the physician chooses to continue working through the findings, device 10 then proceeds to block 82 at block 82 after all the findings have been present which were requested, device 10 returns the physician to block 24.

Referring now to FIG. 10, at block 84 the physician may access additional information in order to rule in or rule out each disease possibility. At block 84 the physician may access the name of the finding represented by each colored bar, additional findings, whose availability is indicated by the colored squares below each column of colored bars, or additional information about any of the above findings. Also at block 84 the physician may also identify and temporarily eliminate non-specific findings, in order to simplify the diagnostic process. The physician may also assign one or more diseases to another category, or temporarily eliminate them from the display and therefore from consideration. Device 10 then proceeds to block 86. At block 86 the physician may move on to the next set of diseases within the same category, select a smaller and/or different group of diseases, select one disease for consideration, for which the findings present are diagnostic, or which he considers the most likely possibility, or go back and continue working through the findings for all the diseases initially generated and not yet eliminated. If the physician chooses to select a smaller and/or different group of diseases, device 10 then proceeds to block 59. If the physician selects one disease for consideration for which the findings present are diagnostic or which he considers the most likely possibility, device 10 then proceeds to block 26. If the physician selects to go back a continue working through the findings for all the diseases initially generated, and not yet eliminated, device 10 then proceeds to block 62.

Figure 11:
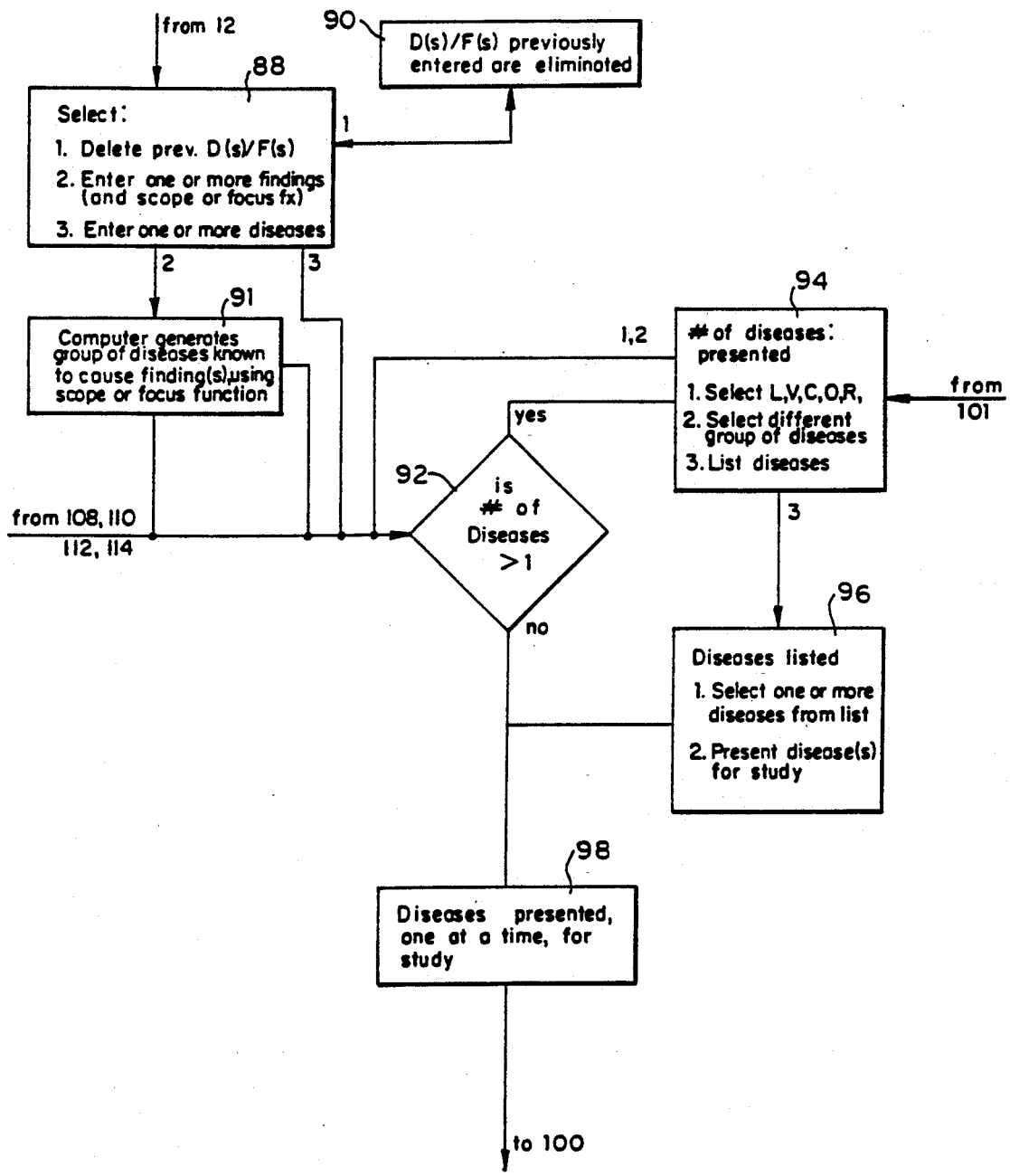

Referring now to FIG. 11, the physician enters the study program at block 88. The physician may delete previously entered diseases or findings, enter one or more findings (and scope or focus findings) or enter one or more diseases. If the physician selects to delete previously entered diseases or findings, device 10 proceeds to block 90 where previously entered diseases or findings are eliminated. If the physician selects to enter one or more findings, device 10 proceeds to block 91 where device 10 generates a group of diseases known to cause the findings using the scope or focus function. Device 10 then proceeds to block 92 where device 10 determines whether the number of diseases generated in block 91 is greater than 1. If the number of diseases is greater than 1, device 10 proceeds to block 94 where device 10 presents the total number of diseases. The physician may then select a subset of diseases (L, V, C, O, R) or the physician may select a different group of diseases, or the physician may select to list the diseases. If the physician selects an L,V,C,O,R subset of diseases, device 10 then proceeds back to block 92 where it is determined whether the number of diseases is greater than 1. If the number of diseases is greater than 1, then device 10 proceeds again to box 94 where the previous maneuvers will be repeated. At block 94, if the physician chooses to select a different group of diseases, device 10 retrieves and presents the finding or set of findings of the name of the disease or group of diseases used to generate the group of diseases he is presently considering, and then returns to and presents the menu used to generate this group of diseases, either the menu ar block 88 or the menu at block 94 or the menu at block 100. At box 94, if the physician selects to list the diseases, device 10 then proceeds to box 96 where the physician may select one or more diseases from the list or he may choose to have the diseases presented for study. Device 10 then proceeds to block 98. At block 92, if only one disease was selected, device 10 proceeds to block 98. At block 98 the disease or diseases are presented one at a time for study. Device 10 then proceeds to block 100 which is described in greater detail in relation to FIG. 9.

Figure 12:
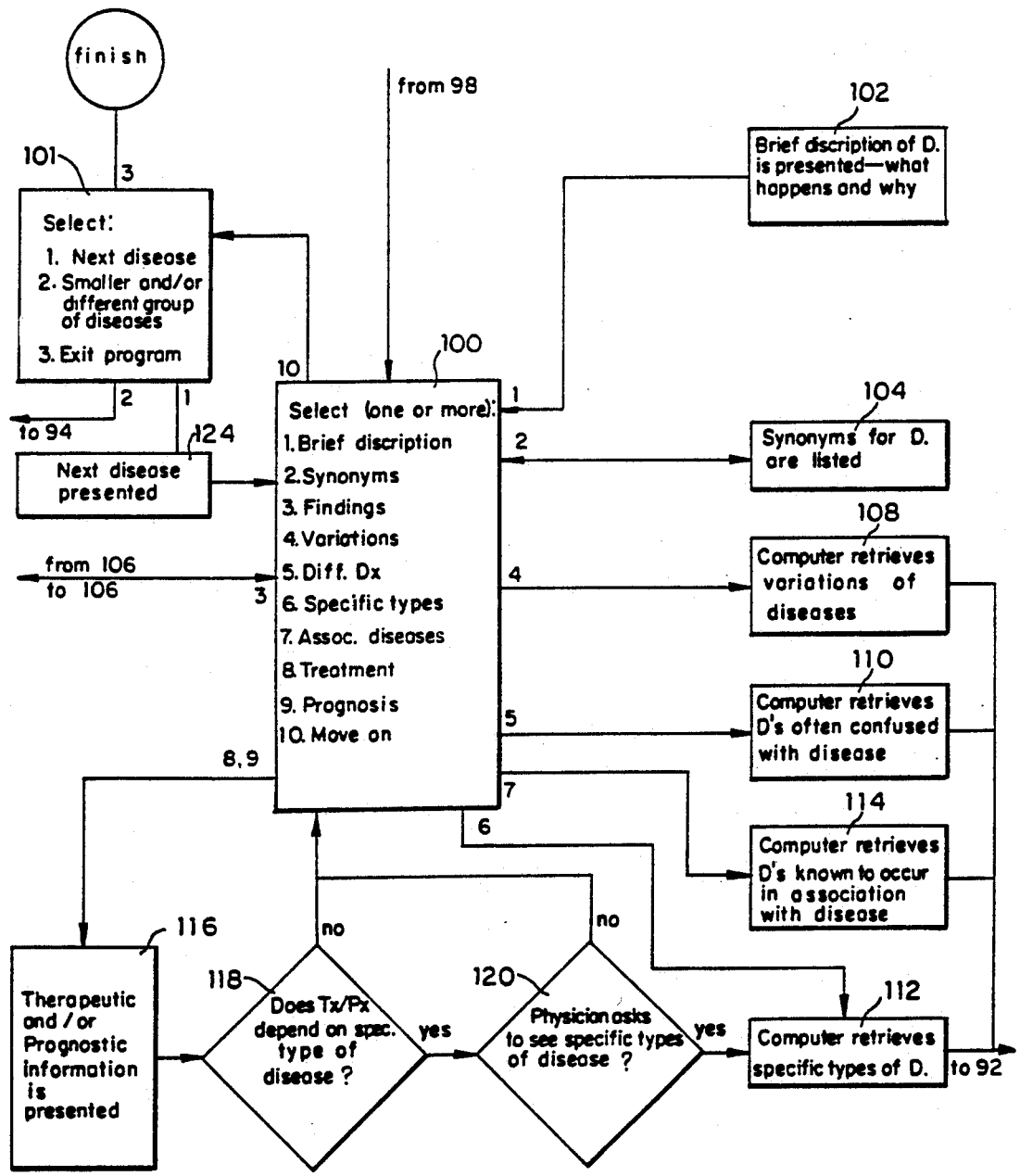

Referring now to FIG. 12, at block 100, the physician may select one or more of the following categories of information about each disease: (1) brief description, (2) synonyms, (3) findings, (4) variations, (5) differential diagnosis, (6) specific types, (7) associated diseases, (8) treatment, or (9) prognosis, or the physician may choose to move on (10). If at block 100 the physician chooses number (1) a brief description of the disease, device 10 moves to block 102 where a brief description of the disease is presented (what happens during the disease and why it happens). If the physician selects number (2) synonyms, device 10 proceeds to block 104 where synonyms for the disease are listed. If the physician selects number (3) findings, device 10 proceeds to block 106 which is described in greater detail in relation to FIG. 10. If the physician chooses number (4) variations, device 1 proceeds to block 108 where device 10 retrieves variations of the disease. Device 10 then proceeds to block 92. If the physician selects number (5) differential diagnosis device 10 then proceeds to block 110 where device 10 retrieves diseases often confused with the disease. Device 10 then proceeds to block 92. If the physician selects number (6) specific types of diseases, device 10 then proceeds to block 112 where device 10 retrieves specific types of diseases. Device 10 then proceeds to block 92. If the physician selects number (7) associated diseases, device 10 proceeds to block 114 where device 10 retrieves diseases known to occur in association with the disease. Device 10 then proceeds to block 92. If the physician selects number (8) treatment or (9) prognosis, device 10 then proceeds to block 116 where therapeutic and/or prognostic information is presented. Device 10 then proceeds to block 118 where it is determined whether the therapeutic and/or prognostic information depends on a specific type of disease. If it is determined that the therapeutic and/or prognostic information depends on a specific type of disease, device 10 proceeds to 120 where the physician may choose to see specific types of diseases. If the physician chooses to see specific types of diseases, device 10 then proceeds to block 112 where device 10 retrieves specific types of diseases. Device 10 then proceeds to block 92. If at 120 the physician does not select to see specific types of disease, device 10 then proceeds to block 100. At 118, if the therapeutic and/or prognostic information does not depend on a specific type of disease, device 10 then proceeds to block 100.

If the physician chooses to move on (10), device 10 moves to block 101. The physician may then (1) move on to the next disease, (2) select a smaller and/or different group of diseases, or (3) exit the program. If the physician chooses to move on to the next disease, device 10 proceeds to block 100. If the physician chooses to select a smaller and/or different group of diseases, device 10 proceeds to block 94. If the physician chooses to exit the program, device 10 exits the program.

Figure 13:
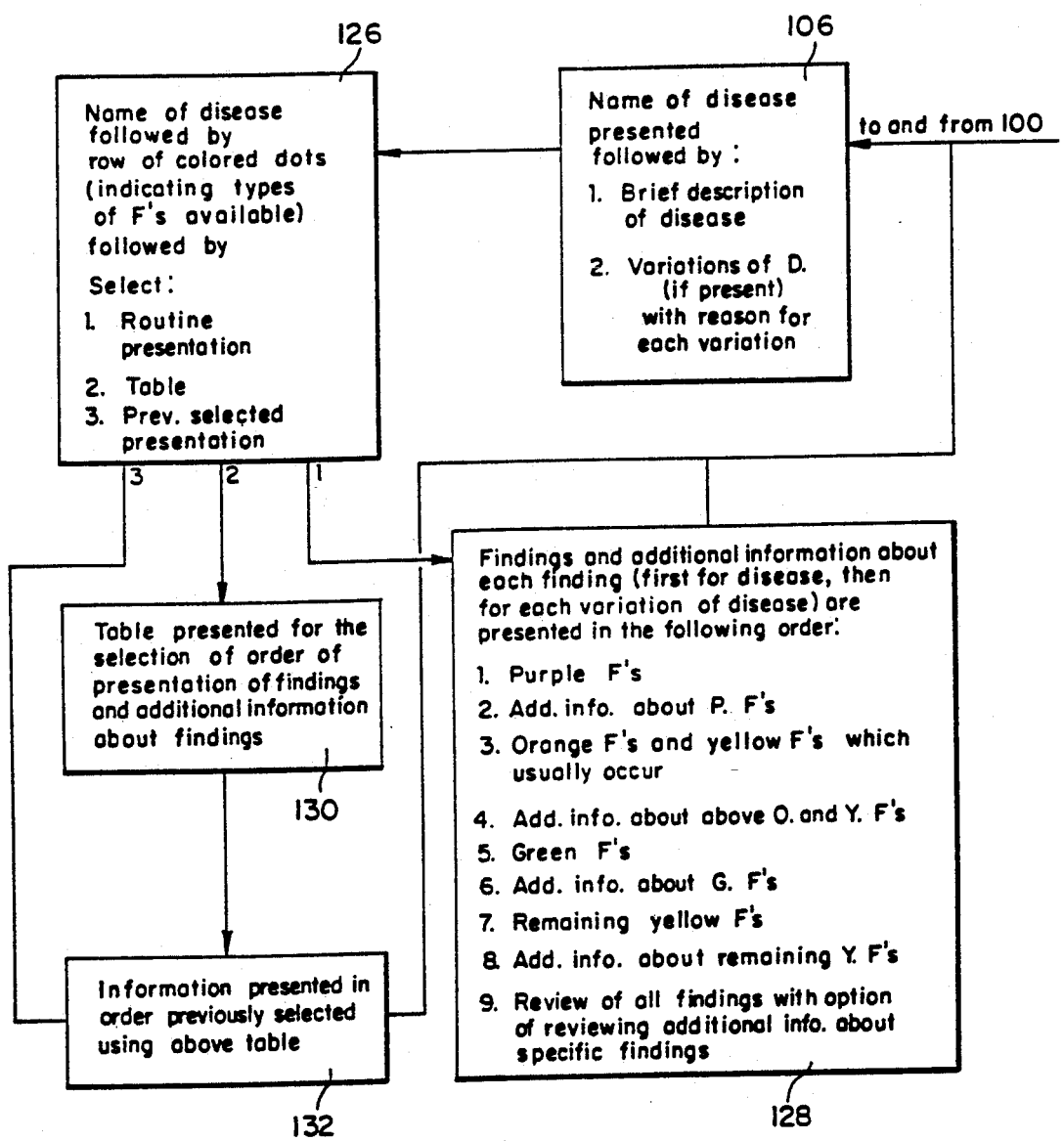

Referring now to FIG. 13, at block 106, device 10 presents the name of the disease followed by a brief description of the disease and variations of the disease (if present) with reason for each variation. Device 10 then proceeds to block 126 where the name of the disease is presented followed by color-coded symbols indicating types of findings available for ruling in or ruling out the disease. Again, at block 126, the physician may choose to have the findings of the disease presented in a routine manner, the physician may select to see a table for selecting a different order of presentation of findings or the physician may select the order of presentation previously selected for, using the table. If the physician chooses to have the findings of the disease presented in a routine order, device 10 then proceeds to block 128. At block 128 the findings and additional information about each finding are displayed in the following order:
1. First Primary Color Findings
2. Additional Information About First Primary Color Findings
3. Second Primary Color Findings and Third Primary Color Findings Which Usually Occur
4. Additional Information About the Above Second and Third Primary Color Findings
5. Fourth Primary Color Findings
6. Additional Information About Fourth primary Color Findings.
7. Remaining Third Primary Color Findings
8. Additional Information About Remaining Third Primary Color Findings.
9. Review Of All Findings With Option of Reviewing Additional Information About Specific Findings Device 10 then proceeds to block 100. At block 126 if the physician selects the table, device 10 proceeds to block 130 where a table is presented for the selection of the order of presentation of findings and additional information about findings. Device 10 then proceeds to block 132 where the findings are presented in the order selected in block 130. Device 10 then proceeds to block 100. If the physician chooses a previously selected order of presentation, device 10 proceeds to block 132 where the information is presented in the order previously selected in block 130. Device 10 then proceeds to block 100.

At various points in the diagnostic and study programs the findings for a disease or diseases are presented to the physician in a color-coded manner. These displays are descried more fully below. For the purpose of illustration only, the examples use preferred colors. It is to be understood that the color-coded findings and diseases may also be displayed by other symbols or test and may be displayed in other formats.

Examples

Example 1

If the physician entered the disease tubal pregnancy at block 14, device 10 will display the color-coded disease findings presented at block 30. Color-coded disease findings of tubal pregnancy are shown in FIG. 14. As shown in FIG. 14, the first primary color symptoms are presented first and are grouped together in a block. In the preferred embodiment of the invention, the heading "PURPLE FINDINGS" and the box around the findings would actually be eliminated. Instead, the findings themselves would appear in the first primary color. The first primary color findings shown are male, negative blood human chorionic gonadotropin (−B-HCG), post hysterectomy (p. hysterectomy), post menopause (p. menopause) and pre-menarchal. The findings post menopause and pre-menarchal are shown with red as a secondary color because the presence of these symptoms should be used with caution in ruling in or ruling out the presence of tubal pregnancy in the patient. Fourth primary color findings are displayed next. In this example, the fourth primary color findings are positive blood human chorionic gonadotropin (+B-HCG) and positive ultrasound/Laprscopy. The finding +B-HCG is shown with a first secondary color which means that this finding is always present with the associated disease. Second primary color findings and third primary color findings which usually occur are displayed next. The second primary color findings shown are female, positive blood human chorionic gonadotropin (+B-HCG), pelvic pain, change from usual menstrual pattern and adnexal tenderness, unilateral. The third primary color findings shown are adnexal mass and 20-30 years old. The second primary color findings female and +B-HCG are shown with a first secondary color which means that these findings are always present with the associated disease. In FIG. 15, other third primary color findings are presented last. In this example the other third primary color findings are predisposing factors of intrauterine device (IUD), previous history (p. Hx) of tubal pregnancy, pelvic inflammatory disease (PID), endometriosis, and infertility. Other third primary color findings are positive (+) culdocentesis, bulging of cul de sac, rectal tenesmus, elevated white blood count (WBC) over 20,000, and decreased hematocrit (HCT). Elevated WBC and Decreased HCT are shown with brosn (Br) as a secondary color. In FIGS. 14 and 15, in a preferred embodiment of the invention, the letters "R", "P", and "Br" would actually appear as red, purple, and brown dots, respectively.

Example 2

The following is an example of how the findings for the disease, tubal pregnancy, might be presented during the execution of the study program. At this point the physician is at block 128. As shown in FIG. 16, the name of the disease is presented, followed by a brief description of the disease. This is a brief statement of what happens as a result of the disease and why. This brief description provides a framework on which to hang the information about the findings. This description is followed by a row of color-coded dots. The first dot is followed by a semicolon, which is followed by four more dots. In one embodiment of the invention, the first dot which is labeled with an "R" would be red. This dot tells the physician that the disease is a life and/or organ threatening emergency. The dots following the semicolon would be purple, orange, yellow and green respectively. They represent the colored sets of findings associated with the disease. This row of dots gives the physician a lot of diagnostic information very quickly. The red dot tells him that the disease must be assumed to be present until proven otherwise, even if there is relatively little evidence to support the diagnosis. The purple dot tells him that there is a way to definitely rule out the disease. The green dot tells him that there is a way to definitely make the diagnosis. (The absence of a green dot would tell him that he will have to make the diagnosis either by exclusion, that is, by ruling out all other disease possibilities, or by comparison, that is, by comparing the evidence for or against the presence of this disease, with that for other diseases.) The orange dot tells him that there findings which, if absent, will help him to rule out the disease. These dots prepare him for what is to come next, the presentation of the findings themselves. The dots following the semicolon may be converted into color-coded numbers if the physician wants to known how many findings are in each colored set.

Example 3

The following is an example of how a physician might use the display presented at block 60 of the bedside diagnostic assistance program to work through a set of disease possibilities. In this example, the physician is using a hand held computer and the bedside diagnostic assistance program, at a patient's bedside, to work through a group of diseases known to cause right lower quadrant abdominal pain, the patient's chief complaint. AT this point he has worked through the following findings for this group of diseases: the purple findings, the orange findings, the yellow findings which usually occur with each disease, and five additional yellow findings for each disease. He is now at block 84 in the above program. At block 59, he selected for a subset of the above diseases: those which has been assigned to the category of likely possibilities or diseases which must be assumed to pe present until proven otherwise. At block 60, the computer presented the first five of these diseases, along with the findings for each disease, using a display employing both text and graphics. This is the display shown in FIG. 3. In Example 3, the first, second, third and fourth primary colors of findings are purple, orange, green and yellow, respectively. The fourth secondary color is green.

FIGS. 17-20 show how a physician might use the above display to work through the displayed diseases. A physician can use the above display to access the following information: 1) the names of the findings represented by the bars, 2) additional findings for each disease, whose availability is indicated by the color-coded boxes at the bottom of the display, and 3) additional information about any of the findings. He can also: 1) identify, and eliminate from the display, the bars representing nonspecific findings, in order to simplify the diagnostic process, or 2) eliminate one or more of the displayed diseases by assigning them to a different category of likeliness. Each of FIGS. 17-20 shows how one or more of the above tasks might be performed, in order to help rule in or rule out the displayed diseases.

Referring to FIG. 17, the computer first identified the finding used to generate the group of displayed diseases—in this case right lower quadrant (abdominal) pain, and which is therefore represented by a bar under each disease name. This is a nonspecific finding, that is, its presence does not make one displayed disease any more likely to be present in the patient than any of the other displayed diseases. The bars representing this finding may therefore be removed from the display, in order to simplify the diagnostic process, without compromising that process. The computer also identifies another finding which is nonspecific, or at least minimally specific, in that it is associated with four of the five displayed diseases. The physician then eliminates the bars which represent these findings.

Referring to FIG. 18, the bars representing right lower quadrant pain and nausea and/or vomiting have been eliminated, and the names of the findings are presented, as shown, in the left lower quadrant of the display. The physician now turns his attention to Disease #1. So far, there is very little evidence to support the diagnosis for this disease (no findings remaining above the line) and a lot of evidence against the diagnosis. Nevertheless, because it is a life and/or organ threatening emergency, it must be assumed to be present until proven otherwise. The physician wants to know if there is a way to definitely rule out this disease. The "P" (or purple) box at the bottom of the display, below the column of bars for this disease, tells him that there is. The physician asks to see the purple finding, or findings, represented by this box. The name of the one purple finding for this disease is presented in the right lower quadrant of the display. The computer also shows him that the opposite of the purple finding is a green finding for this disease. By converting the "G" box next to the above "P" box into a number (not shown) he learns that this is the only green finding for the disease #1. The physician thus learns that the only way to definitely rule out, or rule in, this disease is to operate on the patient. At this point there is not enough evidence supporting the diagnosis for this disease to warrant surgery. The "Y" box at the bottom of the display under the name of this disease tells the physician that there are additional yellow findings for the disease. He accesses these findings to see if there is additional support for the diagnosis. The names of these findings are presented below the purple and green findings. The secondary colors for these findings are also shown. The physician determines (by taking a history from the patient, physically examining the patient, etc.) that only the finding, constipation, is present, and that all the other findings are absent. Having concluded that Disease #1 is a very unlikely possibility he moves on to the next disease, 2nd Disease. The physician could remove Disease #1 from the display, but because it is a life and/or organ threatening emergency, and because he cannot definitely rule it out, he doesn't.

Referring now to FIG. 19, the display now reflects the process just completed for Disease #1. The finding, constipation, which was determined by the physician to be present, is represented by a bar above the line, under Disease #1. The name of the finding appears in the left lower quadrant of the display, and will remain there until the physician asks to have it removed. This finding is also associated with Next Disease, and is therefore represented by a bar above the line, under the name of that disease. Because seven more yellow findings associated with Disease #1 were found to be absent, the "Y=3" box at the bottom of the page, under Disease #1, in FIG. 19, is now a "Y=10" box in FIG. 19. One of those seven findings, diarrhea, is also associated with Last Disease, and is a yellow finding which does not usually occur with that Disease. Therefore, the "Y=1" box under that disease has been changed to a "Y=2" box. If it were, for example, a yellow finding which usually occurred with Last Disease, or an orange finding associated with that disease, a "Yu" bar or an "O" bar would be added below the line under that disease instead. Likewise, no "Yu" bars were added under Disease #1 because none of the above seven findings usually occurs with that disease.

The physician now turns his attention to 2nd Disease. He first asks to see the findings represented by the bars under the name of this disease. These are presented, as shown, immediately below the bars for this disease. The "P" box at the bottom of the display below this disease tells him that there is a way to definitely rule out this disease. He accesses the purple finding for this disease, which is presented as shown. The physician knows that this procedure is very safe and reasonably inexpensive to perform, and that it is a very reliable way to definitely rule out 2nd Disease. Considering the following:

1) The findings which are present for this disease: right lower quadrant pain, change from usual menstrual periods, and +B-HCG (positive blood-human chorionic gonadotropin), taken together, are fairly specific for the disease.

2) 2nd Disease is a life and/or organ threatening emergency.

3) The above procedure (ultrasound), used to definitely rule out 2nd Disease is safe, reasonably inexpensive, and reliable.

The physician decides to order the above procedure before spending any more time looking for more findings. There are no more orange findings, and no matter how many more "Yu" or "Y" findings might be absent, he would still want to definitely rule out the disease. The physician learns from his patient that she just had the above procedure (ultrasound) performed on her less than a week ago by her gynecologist and the result was negative. He knows from past experience that the study does not need to be done again at this time in order to definitely rule out the disease. Having decided that his patient almost certainly does not have 2nd Disease, he eliminates this disease from the display by assigning it to Category E (diseases eliminated from consideration).

Referring now to FIG. 20, 2nd Disease has now been removed from the display. The physician now bypasses Next Disease for the time being. He sees that there are only yellow findings for this disease and that therefore the diagnosis for this disease can only be made by comparison or by exclusion. He therefore decides that he will consider this disease later on, if he can't definitely diagnose another disease. He now turns his attention to 4th Disease. He first asks to see the name of the finding represented by the bar above the line. The "G" dot next to this bar tells him that this finding is very specific for the disease. He is curious about this because so far, other than this one finding, there is very little evidence to support the diagnosis for this disease and a fair amount of evidence against the diagnosis—the absence of two yellow findings which usually occur with this disease, plus the absence of four of the five other yellow findings which he has already looked for (the "Y=4" box for this disease tells him this). The name of the above finding is presented, as shown, immediately below the bars for this disease. The symbol "F+" next to the name of this finding tells him that there are false positive results associated with this test. In order to learn more about the reliability of this test he accesses additional information about this finding. He wants to know only about the reliability of this test. The specific information he requests is presented, as shown, in the right lower quadrant of the display. After studying this information he calls the director of the hospital's laboratory and learns that the results of the test are probably unreliable. He therefore decides that the presence or absence of this finding is undetermined—a reversal of his earlier decision. After accessing the other yellow findings for this disease (not shown) and finding that they are also absent, he indicates to the computer that the presence or absence of the finding, Lab test XYZ, cannot be determined—a change from its previously having been designated as being present. He knows that by doing this, this disease will be automatically removed from the display and reassigned to Category O (other possibilities) according to the computer's rules.

The physician continues to work through the other diseases in this category in the same way as has been described above.

There has been described a computer based medical diagnostic apparatus and method employing color to assist physicians in rendering a diagnosis or studying diseases. The present invention may be embodied in other specific forms without departing from the spirit or essential attributes thereof and, accordingly, reference should be made to the appended claims, rather than to the foregoing specification, as indicating the scope of the invention.

Database

The following is a description of how a database useful in the practice of the invention may be compiled, organized, and stored in the memory area of a computer, in a storage device associated with the computer, or in a storage medium such as a diskette, magnetic tape, etc.

The overall process may be broken down into the following steps: compiling a master list of diseases; compiling a disease Profile ( list of findings) for each disease; compiling a list of synonyms for the name of each disease; compiling a list of synonyms for the name of each finding; and compiling additional information for each disease.

Compiling a Master List of Diseases

Experienced clinicians from each medical specialty (cardiology, neurology, ophthalmology, orthopedic surgery, pediatrics, etc.) will be asked to do the following:

1) compile a complete list of diseases (or injuries) within his specialty—each disease being a definite morbid process or condition having a characteristic set of findings which can be used to more or less rule in, rule out, and/or distinguish that disease from all other diseases, 2) whenever possible, group together diseases having a common set of findings which are characteristic of the group, and 3) use the above set of findings to define a more general disease which represents the above group of diseases and which can be more or less ruled in, ruled out, and/or distinguished from all other diseases (except those within the above group), using that set of findings.

In the listing of all diseases within each medical specialty, each of the above groups of diseases, appears as an indented list of diseases immediately following the general disease which represents the group.

Table 1 shows an example of a partial list of hematological diseases, which have been organized as described above.

TABLE 1

| Anemia |
|---|
| Anemia with normal or decreased reticulocyte count |

TABLE 1-continued

Anemia

Hypochromic, microcytic anemia
Iron deficiency anemia
B thalassemia
Sideroblastic anemia
Macrocytic anemia
Anemia due to vitamin B deficiency
Anemia due to folic acid$_{12}$ deficiency
Normochromic, normocytic anemia
Anemia of chronic inflammation
Anemia of uremia
Anemia of liver disease
Anemia of myxedema
Anemia with increased reticulocyte count
Blood loss anemia
Immunohemolytic anemia
Traumatic hemolytic anemia
Paroxysmal nocturnal hemoglobinuria
Hereditary spherocytosis
Spur-cell anemia
Sickle-cell anemia Diseases in Table 1 are listed in roughly decreasing order of frequency of occurrence.

This initial hierarchical organization of diseases may need to be modified and refined after disease profiles have been compiled for each disease on the list.

Diseases are organized into the above hierarchy so that, in response to one or more entered findings, the computer can first present a relatively small, and therefore manageable, group of general diseases, rather than an overwhelming number of specific diseases. After working through the group of general diseases (more or less ruling in or ruling out each disease), the physician may then move on to the specific diseases represented by those general diseases which have not been eliminated or which appear to be the most likely possibilities.

After a list of diseases for each specialty has been compiled, these lists ar then combined into a comprehensive list of all medical diseases (and injuries) grouped by specialty. This list is hereafter referred to as the master list of diseases.

This master list of diseases is stored in the memory area of a computer in two ways:

Disease File #1

Diseases are stored in the same order in Which they appear on the master list. They are numbered sequentially, from the first disease on the list to the last disease on the list. Four digit numbers are assigned to the most general diseases. Numbers are assigned to the next tier of more specific diseases in the following way: The same four digit number is assigned to each disease as was assigned to the general disease which represents it, followed by a hyphen, followed by a three digit number. Numbers are assigned to each successive tier of more specific diseases in the same way. All digits end in "0" so that a maximum of nine new diseases may be inserted between existing diseases, and numbered, without disrupting the sequential numbering system.

Table 2 shows an example of how the diseases listed in Table 1 might be numbered.

TABLE 2

| | |
|---|---|
| 3150 | Anemia |
| 3150-010 | Anemia with normal or decreased reticulocyte count |
| 3150-010-01 | Hypochromic, microcytic anemia |
| 3150-010-010-010 | Iron deficiency anemia |
| 3150-010-010-020 | β Thalassemia |
| 3150-010-010-030 | Sideroblastic anemia |

TABLE 2-continued

| | |
|---|---|
| 3150-010-020 | Macrocytic anemia |
| 3150-010-020-010 | Anemia due to vitamin 0 deficiency |
| 3150-010-020-020 | Anemia due to folic acid deficiency |
| 3150-101-030 | Normochromic, normocytic anemia |
| 3150-101-130-010 | Anemia of chronic inflammation |
| 3150-010-030-020 | Anemia of uremia |
| 3150-010-030-030 | Anemia of liver disease |
| 3150-010-030-040 | Anemia of myxedema |
| 3150-020 | Anemia with increased reticulocyte count |
| 3150-020-010 | Blood loss anemia |
| 3150-020-020 | Immunohemolytic anemia |
| 3150-020-030 | Traumatic hemolytic anemia |
| 3150-020-040 | Paroxysmal nocturnal hemoglobinuria |
| 3150-020-050 | Hereditary spherocytosis |
| 3150-020-060 | Spur-cell anemia |
| 3150-020-070 | Sickle-cell anemia |

The creation and maintenance of this numbering system, and all other numbering systems in this database, are handled by the computer. The physician or other user rarely if ever needs to see or deal with these numbers.

The above numbers are hereafter referred to as disease position numbers, or DP#'s.

Disease File #2

Diseases are stored alphabetically along with their position numbers. If space in the memory is a limiting factor, only Disease File #2 need be stored in the computer. At any time, all or parts of Disease File #1 can be recreated from Disease File #2, using the above numbering system.

Many diseases will appear more than once on the master list (Disease File #1). That is, the same disease will often be listed under more than one specialty. These duplicate diseases will be eliminated from the alphabetized list (Disease File #2). This may be done in three ways:

1. The computer will check for and eliminate exact duplications. If, when the diseases are arranged alphabetically, the computer discovers that exactly the same name was entered onto the master list more than once, it eliminates the duplicate name or names. The position numbers of the eliminated names are assigned to the one remaining name. The lowest or only position number for each disease is hereafter referred to as the disease number, or D# for each disease.

2. The database compilers and other knowledgeable persons will check for and eliminate synonymous disease names. Each clinician who helped compile the list of diseases for his specialty will identify diseases on his list which he suspects might be included on lists prepared by other specialists. He also indicates the specialties within which these suspected duplicate diseases might be listed. Aided by the above, the compiler will then scan the master list for duplicate diseases, i.e. disease names which are synonymous even though they are not exactly the same. Once identified, these duplicate diseases will be eliminated from Disease File #2, and their position numbers reassigned, by the computer, as described above.

3. Duplicate diseases in Disease File #2, not eliminated by either of the above methods, will be eliminated during the process compiling a list of synonyms for each disease name which is described in detail below.

Compiling a Disease Profile (A List of Findings) for Each Disease

Table 3 shows an example of a form for creating a disease profile using the disease, tubal pregnancy, as an example. The name of the disease is entered at the top of the form. "L" is entered in the first box next to the disease name if the disease is a life and/or organ threatening emergency. "X" is entered if it is not. The letter in the next box indicates the a priori frequency with which the disease occurs in the population in Which the compiling physician practices:
V=very common
O=occasional
C=common
R=rare The findings for the disease are entered in the column below the name of the disease.

The primary color of each finding is entered in the column under "1° COLOR". The secondary color, or colors, are entered in the column under "2° COLOR(S)". The letters in Table 3 corresponding to the primary and secondary colors are as follows:
G=green
O=orange
Y=yellow (a small "u" next to the "Y" indicates that the finding usually occurs with the disease, as apposed to other yellow findings which occur less frequently than that)
P=purple
Br=brown
Bl=blue
R=red The letters entered in the column under "HPLXS" indicate whether the finding is a history finding, a physical finding, a laboratory finding, an x-ray finding, or a special study. Sometimes a finding is more than one of the above. For example, the presence or absence of the finding "IUD" (intrauterine device), may be determined by either taking a history from the patient or by physical examination. During the Bedside Diagnostic Assistance Program, this finding would be presented for consideration, first as a history finding, and then, if for some reason its presence or absence could not be determined as a history finding, again as a physical finding.

The letter entered in the column under "VGH . . ." indicates the type or location of each physical finding.
V=vital sign
G=general appearance (including skin)
H=head and neck
Nr=neurologic
E=extremity
B=back
C=chest
A=abdomen
P=pelvic
R=rectal "X" is entered in the column under "Caused by D." if the finding is caused by the disease. The letter entered in the column under "FREQ" indicates the frequency with which the disease causes the finding, relative to other diseases which cause the same finding: V=very common, C=common, O=occasional, R=rare. The frequency of occurrence may be modified as described below.

A number is entered in the column under "AD. INFO" if the compiling physician wishes to enter additional information about the finding (see below).

TABLE 3

| 2° COLOR(S) | 1° COLOR | L C TUBAL PREGNANCY | HPLXS | VGH ... | CAUSED BY D. | FREQ. | AD. INFO |
|---|---|---|---|---|---|---|---|
| P | G | + B-HCG | L | | X | O | 1 |
| YU | G | + Ultrasound/Laparoscopy for tubal pregnancy | S | | X | V | 2 |
| P | O | Female | H, P | G | | | |
| | O | Pelvic pain | H | | X | C | 3 |
| | O | Change from usual menstrual pattern | H | | X | O | 4 |
| | O | Adnexal tenderness, unilateral | P | P | X | C | 5 |
| | Yu | Adnexal mass | P | P | X | C | 6 |
| | Yu | 20-30 years old | H | | | | 7 |
| | | Predisposing factors ... | | | | | |
| | Y | IUD | H, P | P | | | 8 |
| | Y | p.Hx: Tubal pregnancy | H | | | | 9 |
| | Y | PID | H | | | | 10 |
| | Y | Endometriosis | H | | | | |
| | Y | Infertility | H | | | | |
| | Y | + Culdocentesis | P | P | X | V | 11 |
| | Y | Bulging of cul de sac | P | P | X | C | 12 |
| | Y | Rectal tenesmus | H | | X | O | 13 |
| Br | Y | Elevated WBC (20,000) | L | | X | R | 14 |
| Br | Y | Decreased HCT | L | | X | O | 15 |
| | P | post-Hysterectomy | H, P | P | | | |
| R | P | post-menopause | H | | | | |
| R | P | pre-menarchal | H | | | | |

Findings are entered in the following order:

Green (fourth primary color) findings are entered first. Where appropriate, purple, orange, or yellow are then assigned to these findings as secondary colors. In the Bedside Diagnostic Assistance Program and in the Study Program, green findings with purple as a secondary color are also presented as orange findings with Purple as a secondary color. Green findings with orange or yellow as secondary colors are also presented as orange findings or as yellow findings along with other yellow findings which usually occur. Therefore these green findings need not be entered again as orange or yellow findings.

Orange findings which always occur are then entered and purple is assigned to these findings as a secondary color. Additional orange findings are then entered. Yellow findings which usually occur are then entered. Additional yellow findings are then entered. The opposite of the above green and orange findings which always occur are then entered as purple findings. Additional purple findings are then entered. Where appropriate, red, green, blue and brown are then assigned as secondary colors to the above green, orange, yellow and purple findings. The findings in each colored set are listed roughly in order of decreasing frequency of occurrence, given the disease.

The following rules are preferably used to enter findings:

1. The computer generally treats all words on the same line as one finding.

2. The computer generally allows only one line per finding. That is, words on different lines are treated as different findings.

3. The computer generally considers all words on two or more lines to be one finding if each additional line immediately succeeds the one before it and all but the first line are indented at least three spaces, relative to the first line.

HOWEVER:

4. Two or more findings may be grouped together on the same line, or on successive lines, using the following words or symbols: "and", "or", ",", "/", "±", ";", ":", or ". . . ".

5. The computer understands the above words and symbols to mean the following: "and"=and; "or"=or; ","=and; "/"=and/or; "+"=with or without. ";", ":" and ". . . "are discussed below.

6. Any word or group of words separated by "and", "or", "," or "/" are treated by the computer as separate findings.

7. Any word or group of words preceding 11+11 treated as one finding. All words preceding and following "±"are treated as another finding.

8. If ";" is used, any word or group of words preceding ";" is treated as one finding and all words preceding and following ";" are treated as another finding.

9. If ":" is used, any word or group of words preceding ":" are not treated as a finding. All words preceding and following ":" are treated as a finding.

10. If ". . . "is used, any word or group of words preceding ". . . "is not treated as a finding, but rather as a heading or introduction to the findings which follow ". . . ". Any word or group of words following ". . . "is considered a finding.

11. Any of the above words or symbols may be used in combination.

The following are examples of how the above words and symbols may be used:
NAUSEA and VOMITING"—treated by the computer as two findings.
ELEVATED WBC±LEUKOCYTOSIS—treated by the computer as two findings: ELEVATED WBC and ELEVATED WBC WITH LEUKOCYTOSIS.
ABDOMINAL PAIN; RLQ—treated as two findings: ABDOMINAL PAIN and RLQ ABDOMINAL PAIN.
ABDOMINAL: PAIN AND TENDERNESS—treated as two findings: ABDOMINAL PAIN and ABDOMINAL TENDERNESS.
ABDOMINAL:PAIN
  TENDERNESS
  treated as two findings in the same manner as the immediately preceding example.
RLQ: GUARDING
  TENDERNESS: PERCUSSION/REBOUND
  treated as three findings: RLQ GUARDING, RLQ PERCUSSION TENDERNESS, and RLQ REBOUND TENDERNESS.
ABDOMINAL X-RAY SHOWING:RLQ:
  AIR FLUID LEVELS
  DISTENDED LOOPS OF SMALL BOWEL
  SOFT TISSUE MASS BLURRING THE RIGHT PSOAS SHADOW
  treated as three findings: ABDOMINAL X-RAY SHOWING RLQ AIR FLUID LEVELS; ABDOMINAL X-RAY SHOWING RLQ DISTENDED LOOPS OF SMALL BOWEL, and ABDOMINAL X-RAY SHOWING RLQ SOFT TISSUE MASS BLURRING THE RIGHT PSOAS SHADOW
PREDISPOSING FACTORS . . . AGE GREATER THAN 40
pHx SMOKING
  treated as two findings: AGE GREATER THAN 40 and pHx SMOKING While entering findings, physicians need not worry about strictly adhering to the above rules. This can be done by syntax editors.

Referring again to Table 3, if the physician wishes to add additional information about any of the findings, he enters a number in the column under "AD. INFO". Table 4 shows an example of how additional information might be entered, again using tubal pregnancy as an example.

The additional information on tubal pregnancy provides the following information: describes the finding in more detail; discusses further the significance of the finding; gives the reason for the occurrence of the finding; tells how to elicit the finding, or gives false positives and/or false negatives for the finding, and describes ways in which the finding might erroneously be assumed to be present or absent, or lists and describes other findings which might be confused with the finding.

In the form shown in Table 4, the name of the disease is entered at the top of the page. A number is entered in the column under "NUMBER". This number corresponds to the number entered in the column under "AD.INFO" in Table 3. One or more paragraphs of information are then entered. The letter or letters entered in the column under "DSRHFM" indicate the type of information contained in the adjacent paragraph.

D=detailed description of the finding
S=significance of the finding
R=reason for the finding
H=how to elicit the finding
F=false positives and/or false negatives for the finding
M=miscellaneous information about the finding Indexing the information this way allows for more specific accessing of it.

The above disease profile information is stored in a separate file hereafter referred to as Disease File #3. The disease numbers are stored in sequential order, from the lowest number to the highest number. The following information is stored next to each disease number:

1. L or X and L,V,C or R, which indicate whether or not the disease is a life and/or organ threatening emergency, and the a priori frequency of occurrence of the disease;

2. The finding numbers for the findings in each disease profile, listed in the same order in which the findings were compiled; and
3. Next to each finding number:
   a) P,G,O,Yu or Y (the primary color of the finding)
   b) One or more: P,G,O,Y,Bl,Br,R (secondary colors)
   c) One or more: H,P,L,X,S (history finding, physical finding, lab finding, etc.)
   d) V,G,H ... (type or position of physical findings)
   e) V,C,O or R, if the finding is caused by the above disease (the frequency with which the disease causes the finding relative to other diseases—see above)

Explanation of Table 5
Finding = the number of (these are actually five digit numbers, as set forth in detail below. 1° color = the primary color of the finding. HPLXS = history finding, physical finding, lab finding, etc.. VGH ... = type or location of physical finding: vital sign, general appearance, etc. L,X (disease) = life and/or organ threatening emergency, or not. Freq. D F = frequency with which disease causes finding relative to other diseases. VCOR (disease) = a priori frequency of occurrence of disease. Disease = the number of the disease (see above).

According to the rules which govern the preferred order of presentation of findings the above findings would be presented in the following order:

TABLE 4

| DSRHFM | NUMBER | TUBAL PREGNANCY |
|---|---|---|
| DSF | 1 | The radioimmunoassay for the B-subunit of human chorionic gonadotropin is specific and highly sensitive. This test can detect pregnancy a day or two after implantation. Pregnancy can be diagnosed before the first missed period. The test can measure the minute amounts of hCG secreted with ectopic pregnancy, while most other pregnancy tests are negative in at least 50% of cases. Only two conditions can give rise to a positive test besides pregnancy: choriocarcinoma and hydatidiform mole. |
| DF | 2 | Pelvic ultrasound is diagnostic for tubal pregnancy if: 1) B-hCG is positive and 2) there is a mass (conceptus) in the tube and an empty uterus. There are several false positive and false negative results. The reliability of this test depends on the expertise of the radiologist who interprets the sonogram. |
| DS | | Laparoscopy may be used to diagnose tubal pregnancy by direct visualization of the impregnated tube. It is a relatively minor procedure, performed routinely by gynecologists. Laparoscopy decreases the usual 20% chance of finding no tubal pregnancy on laparotomy to only about 4–5%. It should be considered whenever the clinical picture and/or ultrasound is inconclusive. |
| R | 3 | Pelvic pain is due to stretching of the fallopian tube, separation of the placenta, blood in the peritoneal cavity, rupture of the tube, etc. |
| D | | The patient may report: 1) mild intermittent fleeting episodes 2) irregular episodes of moderate pain lasting several hours to several days 3) sudden severe pain 4) etc. |
| D | 4 | This is typically reported by the patient as an absence of her normal period followed by irregular episodes of slight vaginal bleeding (spotting). However, the patient may report: a missed period with no subsequent vaginal bleeding, early or late period, increased or decreased flow with last period |

During the Bedside Diagnostic Assistance Program, after generating a list of diseases for consideration, the computer then presents the findings for these diseases to the physician, who, by determining the presence or absence of each finding, rules in or rules out each disease possibility. These findings are presented in a useful sequence (this sequence is described in detail in the description of the Bedside Diagnostic Assistance Program). In order to present the findings in this sequence, the computer organizes the above disease profile information into a table of data. Table 5 shows an example of what such a table might be like.

TABLE 5

| Finding # | 1 | 2 | 3 | 4 | 5 | 6 | 7 | 8 | 9 |
|---|---|---|---|---|---|---|---|---|---|
| 1° color | Y | P | O | P | Yu | O | Y | Y | Y |
| HPLXS | X | H | P | H | L | H | P | S | H |
| VGH ... | | | H | | | | V | | |
| L, X (disease) | X | L | X | X | X | L | X | X | X |
| Freq. D F | C | O | V | V | C | O | V | V | O |
| VCOR (disease) | R | O | V | C | C | C | V | C | R |
| Disease # | (not shown) | | | | | | | | |

Finding #2: PH LOO (a purple, history finding, for a life/organ threatening emergency which occasionally causes the finding relative to other diseases, and which occurs occasionally)
Finding #4: PH XVC (a purple, history finding, for a disease which is not a life/organ threatening emergency, which very frequently causes the finding, and which occurs commonly)
Finding #6: OH LOC
Finding #3: OPHXVV
Finding #5: YuL XCC
Finding #9: YH XOR
Finding #7: YPVXVV
Finding #1: YX XCR
Finding #8: YS XVC The Table 5 is one of a multiplicity of tables which the computer can create, ad hoc, for various purposes.

A separate file is created for the additional information about each finding, hereafter referred to as the Findings: Additional Information File. In this file the finding numbers are stored sequentially. Next to each finding number is the disease number for the disease associated with the finding, followed by the additional information about the finding for that disease, indexed as shown above.

The findings themselves are stored in three ways:

Finding File #1

The findings are stored in numerical order. The findings are entered into the computer as disease profiles are created for each disease. Five digit numbers are used. The findings are numbered sequentially from the first finding entered to the last finding entered. The disease number for the disease associated with each finding is stored next to each finding.

Finding File #2

Findings are stored in alphabetical order. The above finding numbers and disease numbers are stored next to their respective findings. If, when the findings are filed alphabetically, the computer finds two or more findings with exactly the same name, it eliminates the duplicate findings. The disease number associated with each eliminated finding is assigned t the remaining finding (the remaining finding now has two or more associated disease numbers). The finding numbers associated with the eliminated findings are stored and assigned to new findings as they are entered.

Finding File #3

This is a categorical listing of findings which is described later.

Compiling a List of Synonyms for the Name of Each Disease

Each disease name from Disease File #2 (alphabetical list) is presented by the computer to a physician or other person knowledgeable in medical terminology who then compiles approximately five to fifteen synonyms for each name. Medical textbooks will be used to help compile as comprehensive a list as possible for each disease name. Each group of synonyms is then entered into the computer, including the disease name initially presented by the computer (the name from Disease File #2) which is marked with an "*". The computer then checks each synonym for correct spelling; assigns the disease number (from Disease File #2) associated with the name marked with an "*" to each synonym in the group; and designates the shortest synonym in each group as the representative synonym for the group and marks it with an "R".

All synonyms for all diseases are stored in a file hereafter referred to as the Disease Synonym File. They are stored in alphabetical order, along with the disease numbers which have been assigned to them (above). Each disease name in Disease File #1, and Disease File #2, is replaced with the same numbered "R" synonym in the Disease Synonym File.

If, when the synonyms are stored alphabetically, the computer discovers two synonyms which are exactly the same, it checks to see if they have the same disease number. If they have the sane disease number, one of them is eliminated. If they have different disease numbers, then all the synonyms in the file associated with each disease number are presented (grouped by disease number) to a physician or other person knowledgeable in medical terminology who then combines all the synonyms from both groups into one new group (this is what is usually done), or creates two or more new groups of synonyms. If all the synonyms from both groups are combined into one group, the lower disease number is assigned to them. The shortest synonym in the group is designated as the "R" synonym (representative synonym) for the group. If the new "R" synonym for the group is different from the old "R" synonym with the lower disease number, then the lower numbered old "R" synonym is replaced with the new "R" synonym in Disease File #1, and Disease File #2.

The disease profile information in Disease File #3 and in the Findings: Additional Information File, for the higher numbered old "R" synonym and for the new "R" synonym, is presented to a physician or other knowledgeable person who must then combine these two disease profiles into one new disease profile. In stepwise fashion, the old disease profile information for both the higher numbered old "R" synonym and the new "R" synonym is then eliminated from the following files: Findings: Additional Information File, Finding File #3, and #2, Finding File #1, and Disease File #3. The higher numbered old "R" synonym is then eliminated from Disease File #1 and Disease File #2. The disease position numbers in Disease File #2 associated with the higher numbered old "R" synonym are reassigned to the new "R" synonym. The new disease profile information for the new "R" synonym is then entered into the computer and stored in the above listed files.

If two new groups of synonyms are created (above) then the two disease numbers are reassigned to these synonyms accordingly, and then the shortest synonym in each group is designated as the "R" synonym for each group. If the old "R" synonyms are different from the new "R" synonyms, then they are replaced in Disease File #1 and Disease File #2 with the same numbered new "R" synonyms. No other changes in the data files need to be made.

If more than two new groups of synonyms are created (this would rarely happen), then the process is the same as if two groups had been created except that the new "R" synonym for the third group (without a disease number) must be entered into the computer as a new disease, along with a disease profile and a complete list of synonyms for that disease (including the synonyms in this third group).

The overall process insures that a particular disease can be accessed using any of its names, and each disease is represented by only one disease name, number and profile throughout the database, except for the Disease Synonym File. So long as enough synonyms are compiled for each disease, it is highly unlikely that two different groups of synonyms would exist for the same disease, without at least one name in each group being identical to a name in the other group. It is preferable to eliminate synonymous disease names from the database before disease profiles are compiled.

Compiling a List of Synonyms for Each Finding

A hierarchical list of finding categories is first created. These categories, unlike the above disease categories, are not findings themselves, but are categories to which all possible findings could be assigned. Table 6 shows an example of what part of this list of categories might look like.

TABLE 6

History findings
Organ systems
Cardiovascular

TABLE 6-continued

Pulmonary
Gastrointestinal
Etc.
Anatomical
Head and neck
Hair
Scalp
Face
Eye
Etc.
Chest
Back
Abdomen
Etc.
Physical findings
Vital signs
General appearance
Head and neck
Neurological
Chest
Inspection
Auscultation
Heart sounds
Lung sounds
Etc.
Percussion
Etc.
Back
Abdomen
Etc.
Laboratory findings
Hematology
Chemistry
Bacteriology
Etc.
EKG findings
X-ray Findings
Skull
Facial
Etc.
Special Studies Findings are assigned to these categories by the compiler during the process of compiling a list of synonyms for each finding (see below). The computer assigns a unique number to each category, which it then uses to locate the findings which are stored alphabetically within each category. This categorical listing of findings is hereafter referred to as Finding File #3. This categorical listing of findings is more meaningful, and more useful to physicians and other users than the numerical or alphabetical listings contained in Finding File #1 and Finding File #2. It also allows physicians or other users to perform certain judgmental tasks which a computer is not capable of performing.

After this list of finding categories has been created and entered into the computer, a list of synonyms is compiled for each finding in the following way.

The name of each finding in Finding File #2 (alphabetical list) is presented by the computer to a physician or other knowledgeable person who compiles a list of approximately five to thirty synonyms for each name. The number of synonyms required for each finding depends on: 1) the number of words in the longest name of the finding, and 2) the number of generally accepted synonyms for each word in that name. Medical dictionaries and other synonym tables may be consulted to compile comprehensive lists of synonyms for each finding. Common abbreviations for each finding name are included in each list of synonyms. Each abbreviation is marked with an "a". Each group of synonyms is then entered into the computer, including the finding name initially presented by the computer (the name from Finding File #2) which is marked with an "*". The computer then: checks each synonym for correct spelling, assigns the finding number (from Finding File #2) associated with the name marked with an "*" to each synonym in the group, designates the shortest non-abbreviated synonym as the representative synonym for the group and marks it with an "R", and designates the shortest abbreviation as the representative abbreviation for the group and marks it with an "Ra". All synonyms for all findings are stored in a file hereafter referred to as the Finding Synonym File. They are stored in alphabetical order along with the finding numbers assigned to them.

Each finding name in Finding File #1 and Finding File #2 is replaced with the same numbered "R" synonym in the Disease Synonym File. The "Ra" synonym for each finding is stored next to the same numbered "R" synonym in Finding File #2. (During the execution of the Bedside Diagnostic Assistance Program or the Study Program, if requested by the physician, for brevity sake, these "Ra" synonyms are presented instead of the "R" synonyms. If, when it is presented to him, the physician is not familiar with the "Ra" synonym for a particular finding, he may quickly access the "R" synonym for that finding.)

Each "R" synonym from Finding File #2 is then presented to the compiler who enters the name under one or more appropriate categories in Finding File #3. The computer then arranges the names in alphabetical order (within each category), stores the associated finding number (from Finding File #2) next to each, and stores the number of the category to which each was assigned, next to the same "R" synonym in Disease File #2. (While a compiler decides which category, or categories, each "R" synonym is assigned to, the actual transfer of these "R" synonyms and their associated finding numbers from Finding File #2 to Finding File #3, and the transfer of category numbers from Finding File #3 to Finding File #2 is performed by a computer in order to insure that these transfers are done accurately.) If, when the synonyms are stored alphabetically in the Finding Synonym File, the computer discovers two synonyms which are exactly the same, it checks to see if they have the same finding number. If they have the same finding number, one of them is eliminated. If they have different finding numbers, then all the synonyms in the Finding Synonym File associated with each finding number are presented (grouped by finding number) to the compiler, who then combines all the synonyms from both groups into one group, or creates two or more new groups of synonyms. If all the synonyms from both groups are combined into one group, the lower finding number is assigned to them. The shortest synonym in this new group is designated as the "R" synonym for the group. The shortest abbreviation in the group is designated as the "Ra" synonym for the group. If the new "R" synonym for the group is different from the lower numbered old "R" synonym, then the lower numbered old "R" synonym is replaced with the new "R" synonym in Finding File #1, Finding File #2, and Finding File #3. If the new "Ra" synonym is different from the lower numbered old "Ra" synonym, then the lower numbered old "Ra" synonym is replaced with the new "Ra" synonym in Finding File #2. If the new "R" synonym is different from the higher numbered old "R" synonym, then the name and/or number of the higher numbered old "R" synonym is:

1) eliminated from Finding File #1 and its associated disease number, or numbers are reassigned to the new "R" synonym;
2) eliminated from Finding File #2 and its associated disease and category numbers are reassigned to the new "R" synonym and its associated "Ra" synonym is eliminated;
3) eliminated from Finding File #3;
4) replaced with the new "R" synonym number in Disease File #3 (disease profiles), and
5) eliminated from the Findings: Additional Information File and the associated disease number (or numbers) and the additional information about the finding for the disease (or diseases) is stored next to the new "R" synonym number.

The higher finding number (the number of the higher numbered old "R" synonym) is stored and assigned to new findings as they are entered into the database.

If two new groups of synonyms are created then the two finding numbers are reassigned to these synonyms accordingly. The shortest synonym in each group is designated as the "R" synonym for the group, and the shortest abbreviation in each group is designated as the "Ra" synonym for the group. Any old "R" or "Ra" synonym, whose number was not changed, is handled in the same way as the lower numbered old "R" or "Ra" synonym, above. Any old "R" or "Ra" synonym, whose number was changed, is handled in the same way as the higher numbered old "R" or "Ra" synonym, above. If more than two new groups of synonyms are created, the process is the same as above except that, after the two numbers have been assigned to the two largest groups of synonyms, the additional unnumbered synonyms are eliminated from the Finding Synonym File.

Each synonym in the Finding Synonym File is also compared with each finding name in Finding File #2 for which a list of synonyms has not yet been compiled. The name and/or number of each finding in Finding File #2 which is identical to a synonym in the Finding Synonym File is:

1) eliminated from Finding File #1 and Finding File #2 and its associated disease number, or numbers, are then re-assigned to the "R" synonym which has the same finding number as the above synonym,
2) replaced with the new "R synonym number in Disease File #3 (disease profiles), and
3) eliminated from the Findings: Additional Information File and the associated disease number (or numbers) and the additional information about the finding for the disease (or diseases) is stored next to the new "R" synonym number.

Again, the finding number for the eliminated finding name is stored and later assigned to a new finding when it is entered into the database. The above findings in Finding File #2 are thus eliminated before a list of synonyms for each of these findings is unnecessarily compiled.

If, when a finding from Finding File #2 is presented to the compiler, he suspects that it is synonymous with a group of synonyms in the Finding Synonym File, even though it is not exactly the same as one of them, he may compile and enter short lists of synonyms (approximately five at a time) until:

1) one of the synonyms in these lists is identical to a previously entered synonym in the Finding Synonym File and/or
2) the total number of synonyms entered or the total number of synonyms in the group generated by combining the synonyms entered with those already contained in the Finding Synonym File is equal to the number required for that finding (depending on the number of words in the longest name of the finding and the number of generally accepted synonyms for each word in that name).

The overall process ensures that all synonymous finding names which are compiled into disease profiles and entered into the database are recognized by the computer as being synonymous. This, in turn, insures that when, during the execution of the Bedside Diagnostic Assistance Program or the Study Program, a particular finding is entered (the patient's main or initial presentation or a presentation commonly encountered in the physicians practice), the computer will generate a comprehensive list of diseases known to cause that finding. Again, so long as enough synonyms are entered for each finding, it is highly unlikely that two different groups of synonyms would exist for the same finding, without at least one name in each group being identical to a name in the other group.

The above process also causes each finding to be represented by only one name throughout the database, except for the Finding Synonym File.

A list of findings which would automatically be present or absent, given the presence or absence of each finding in Finding File #2, is compiled in the following two ways. The computer presents each finding in Finding File #2 to a physician or other knowledgeable person and marks it with a "+". The person then enters the opposite of the finding and marks it with a "—". The person then compiles a list of synonyms for each opposite finding as described above.

The computer again presents each finding in Finding File #2 to a physician or other knowledgeable person and marks it with a "+". He then searches through one or more appropriate categories in Finding File #3 for findings which would automatically be present, given the presence of the above finding. He enters these findings under the above finding and marks each with a "+". He then searches for, enters, and marks with a "—", findings which would automatically be absent, given the presence of the above finding. Findings which would automatically be present, and absent, given the absence of each finding in Finding File #2 are compiled in a similar way. The above information is stored under each finding in Finding File #1.

Compiling Additional Information For Each Disease

Table 7 shows an example of how the following information about the disease, acute gastroenteritis, might be compiled. A brief description of the disease (what happens and why), therapeutic information and prognostic information are presented. The name of the disease is entered at the top of the page. The letters entered in the column under "DTP" indicate the type of information contained in the adjacent paragraph or paragraphs: D=brief description; T=therapeutic information; P=prognostic information. An "X" is entered in the column under "HEADINGS" if a word or phrase on the same line is a heading or introduction to the information contained in the subsequent paragraph or paragraphs. The word or phrase used as a heading must be followed immediately by a ":". One or more specific headings may be entered under a more general heading. This is done by indenting them at least three the spaces relative to the more general heading. The use of headings allows for more specific accessing of information. For example, if a physician asks to see the therapeutic information for acute gastroenteritis, the computer first presents the most general headings for that information: "General treatment" and "Specific treatment". If he then asks to see the information under "General treatment", the computer first presents the more specific headings under this more general heading: "Control of vomiting", "Control of diarrhea", and "Replacement of fluid and electrolytes". He may then select the information under any or all of these more specific headings.

If treatment or prognosis depends on which specific type of a disease is present in a patient, then the compiling physician lists those specific types of disease. He may refer to the master list of diseases (Disease File #1) in doing this. However, he may need to modify whichever list of specific diseases he finds on the master list. A list of specific diseases which is useful for diagnosis may not be useful for treatment or prognosis. An "S" is entered in the column under "HEADINGS" next to the first disease on the list. This tells the computer to present these diseases for diagnostic consideration or for study (if requested by the physician) during the execution of the Bedside Diagnostic Assistance Program or the Study Program. Any specific diseases entered at this time, which are not already contained in the database, must be entered as new diseases, along with a disease profile, a list of synonyms, and other additional information for each disease.

The above descriptive, therapeutic, and prognostic information for diseases is stored in a file hereafter referred to as the Diseases: Additional Information File. The above information for each disease is stored under its disease number. The numbers are ordered sequentially, from the lowest number to the highest number.

ity of the disease, etc.) In the example, the presentation of tubal pregnancy is quite different after tubal rupture has occurred.

D = The differential diagnosis for the disease (diseases which are often confused with the disease)

Co = Complications (diseases which are caused by the disease)

Ca = Causes of the disease (diseases which are known to cause the disease, directly or indirectly)

A = Associated diseases (diseases which are known to occur more frequently in association with the disease than otherwise, even though no known causal relationship exists between the diseases)

TABLE 8

| VDCoCaA | PREGNANCY TUBAL PREGNANCY |
|---|---|
| V | Ruptured tubal pregnancy |
| D | Corpus luteum of early pregnancy |
|  | Spontaneous abortion |
|  | Pelvic inflammatory disease |
|  | Ruptured ovarian cyst |
|  | Appendicitis |
|  | Torsion of ovarian cyst |
|  | Etc. |
| Co | Hemorrhagic shock |
|  | Hemorrhage: Pelvic |
|  | Intraabdominal |
|  | Adhesions: Pelvic |
|  | Intraabdominal |
|  | Small bowel obstruction |
|  | Infertility |
|  | Etc. |
| Ca | Idiopathic |
|  | Pelvic inflammatory disease |
|  | Endometriosis |
|  | Etc. |
| A | Infertility |

As shown in Table 8, tubal pregnancy is known to

TABLE 7

| DTP | HEADINGS | ACUTE GASTROENTERITIS |
|---|---|---|
| D |  | Acute gastroenteritis is acute inflammation of the mucosal surface of the gastrointestinal tract . . . |
| T | X | General treatment: Therapy is directed toward controlling vomiting and/or diarrhea and replacing the fluids and electrolytes lost as a result of vomiting arid/or diarrhea. |
|  | X | Control of vomiting: Several drugs may be used to control nausea or vomiting, including . . . Control of diarrhea: Judicious control of the patient's diarrhea . . . |
|  | X | Replacement of fluid and electrolytes: An assessment of the patient's fluid and electrolyte losses and his acid-base status . . . |
|  | X | Specific treatment: This depends on the specific type of disease present in the patient. |
|  | S | Viral gastroenteritis Bacterial gastroenteritis: Salmonella Shigella Etc. |
| P | X | Prognosis: This depends on the specific type of the disease . . . |

Table 8 shows an example of how information about certain disease relationships is compiled. The disease, tubal pregnancy is used as an example. The above information is compiled for each disease in Disease File #2. The name of the disease is entered at the top of the page. The letters entered into the column under "VDCoCaA" indicate the relationship of the diseases in the adjacent list to the disease at the top of the page:

V = Variations (presentations of the disease which differ from the typical presentation, due to the age of the patient, the duration of the disease, the severoccur more frequently in women with a history of infertility, even though infertility itself is not known to cause tubal pregnancy. Tubal pregnancy is also known to cause infertility, however, as shown in Table 8.

The diseases in each list are listed roughly in order of decreasing frequency of occurrence. The rules which must be adhered to when entering diseases onto the above form are similar to the rules which govern the entering of findings onto the disease profile form (see above). Again, any diseases in these lists which are not already contained in the database must be entered as new diseases, along with a disease profile, a list of synonyms, and other additional information for each disease.

The above information is stored in a file hereafter referred to as the Disease Relationship File. The disease numbers for the diseases in Disease File #2 are stored sequentially (from the lowest number to the highest number). The above information for each disease is stored next to its disease number, in essentially the same order in which it is entered (as shown in Table 8). The diseases in each list are represented by their disease numbers rather than their names, however.

The above information is retrieved and presented by the computer during the execution of the Bedside Diagnostic Assistance Program and the Study Program in ways, and for purposes, which have been described elsewhere herein.

The following is a list of all the files contained in the database, with a brief description of the content of each file.

Disease File #1: Diseases are stored in the same order in which they appear on master list of diseases. The diseases are numbered sequentially as shown above. The same disease may appear in more than one place on this list. However, each disease is represented by only one name. The number next to each disease name is the position number for that name. The lowest position number for each name is the disease number for the disease represented by that name.

Disease File #2: Diseases are stored in alphabetical order. Each disease is represented by only one name, the "R" synonym from the Disease Synonym File, and each disease name appears only once in this alphabetical listing. The disease number for each disease and any additional position numbers (if they exist) for each disease are stored next to each disease name.

Disease File #3: Disease profile information is stored in this file. The above disease numbers are stored in sequential order. The following information is stored next to each disease number:

1. L or X, and V,C,O or R (these letters indicate whether or not the disease is a life and/or organ threatening emergency, and the a priori frequency of occurrence of the disease),
2. The finding numbers for the findings associated with the disease, stored in the same order in which the findings were compiled,
3. Next to each finding number:
    a) P,G,O,Yu or Y (the primary color of the finding)
    b) P,G,O,Y,Bl,Br,R (one or more secondary colors)
    c) H,P,L,X,S (the finding type—one or more)
    d) V,G,H . . . (the type or location of physical findings)
    e) V,C,O or R (if the finding is caused by the disease, the frequency with which the disease causes the finding, relative to other diseases)

Disease Synonym File: All synonyms for all diseases are stored in alphabetical order. The representative synonym for each disease is marked with an "R". These "R" synonyms are the disease names which appear in the above disease files. The disease number (see Disease File #1 and Disease File #2 above) associated with each synonym is stored next to each synonym.

Diseases: Additional Information File: The disease numbers for all diseases are stored sequentially (from the lowest number to the highest number). Next to each disease number the descriptive, therapeutic, and prognostic information for that disease is stored in essentially the same order in which it was entered (see Table 7). The specific disease types, listed within the therapeutic and/or prognostic information for each disease, are represented by their disease numbers, rather than by their names.

Disease Relationship File: The disease numbers for all diseases are stored sequentially as above. The following information is stored next to each disease number:

1) V,D,Co,Ca,A (one or more of the following letters or pairs of letters, each of which indicates a particular disease relationship and, 2) next to each of the above letters, or pairs of letters, a list of diseases having that relationship to the above disease (the diseases in these lists are represented by their disease numbers rather than by their names).

Finding File #1: All finding numbers are stored sequentially (from the lowest number to the highest). The name of each finding is stored next to its finding number. Each finding occurs only once in this file. The disease number for each disease associated with each finding (see disease profiles above) is stored next to the name of each finding. (One or more diseases are associated with each finding). Other findings automatically present or absent are also stored here.

Finding File #2: The names of all findings are stored in alphabetical order. Each finding occurs only once in this file and each finding is represented by only one name. The following information is stored next to each finding name:

1) The "Ra" synonym for the finding (see below)
2) The finding number for the finding
3) The number of each disease associated with the finding
4) The number of each category to which the finding is assigned in Finding File #3.

Finding File #3. Finding categories are listed and numbered is marked with an "R". The representative abbreviation for each finding is marked with an "Ra". The above "R" synonyms are the finding names which are stored in the above finding files. The above "Ra" synonyms are stored in Finding File #2. The finding number associated with each synonym is stored next to each synonym (each finding number is associated with many synonyms).

Findings: Additional Information File: The finding numbers for all findings are stored sequentially. The following information is stored next to each finding number:

1. The number of each disease associated with the finding;
2. Next to each disease number, the additional information about the finding for that disease, indexed as shown in Table 4.

The above database should allow the computer to very quickly and accurately retrieve and present whatever information is needed during the execution of the Bedside Diagnostic Assistance Program or the Study Program. It should also allow the computer to create, ad hoc, a multiplicity of files and/or tables in order to perform whatever tasks are required during the execution of those programs.

At various points in the diagnostic and study programs the findings for a disease or diseases are presented to the physician in a color-coded manner. These displays are described more fully below. For the purpose of illustration only, the examples use preferred colors. It is to be understood that the color-coded findings and diseases may also be displayed by other symbols or test and may be displayed in order formats.

I claim:

1. A method of presenting medical information for diagnosis and study of disease, comprising the following steps:
   (a) entering into a processing means data indicative of at least one finding or one disease;
   (b) displaying on a color display coupled to the processing means:
      (i) in response to entered data indicative of a finding, the name of at least one disease known to cause the finding and for each disease displayed, findings known to be associated therewith,
      (ii) in response to entered data indicative of a disease, the name of at least one finding known to be associated with the disease,
   the displayed findings of each disease being color coded according to the significance of the presence or absence of each finding in ruling in or ruling out the possibility of the disease being present.

2. The method of claim 1 wherein the color-coded findings of each disease are displayed in at least one group wherein same color bindings are presented in the same group.

3. The method of claim 1 wherein the finding is displayed as a color-coded symbol representing the name of at least one finding.

4. The method of claim 1 wherein displayed diseases are color-coded according to the following rule:
   a first color is assigned to diseases that are life-threatening or organ-threatening emergencies.

5. The method of claim wherein the findings of each disease are color-coded according to the following rules:
   (i) the first primary color is assigned to findings that are never present with a given disease;
   (ii) the second primary color is assigned to findings that are at least almost always present with a given disease;
   (iii) the third primary color is assigned to findings, other than second primary color findings, which are generally specific for, but not diagnostic for, a given disease;
   (iv) the fourth primary color is assigned to findings that are diagnostic for a given disease.

6. The method of claim 5 wherein the findings of the disease are further coded with at least one secondary color code that indicates the significance of the presence or absence of the findings associated with them in ruling in or ruling out the disease associated with the finding.

7. The method of claim 6 wherein the secondary color code is applied to the findings of diseases according to the following rule:
   a first secondary color is assigned to second primary color findings and fourth primary color findings if these findings are always present with associated diseases, and the opposite of said second primary color and fourth primary color findings are then presented as first primary color findings.

8. The method of claim 7 wherein said first secondary color is the same color as said first primary color.

9. The method of claim 6 wherein the secondary color code is applied to the findings of the diseases according to the following rule:
   a second secondary color is assigned to fourth primary color findings if these findings are almost always present with associated diseases and said fourth primary color findings are also presented as second primary color findings.

10. The method of claim 9 wherein said second secondary color is the same color as said second primary color.

11. The method of claim 6 wherein the secondary color code is applied to the findings of the diseases according to the following rule:
    a third secondary color is assigned to fourth primary color findings if these findings usually occur with associated diseases and said fourth primary color findings are also presented as third primary color findings.

12. The method of claim 11 wherein said third secondary color is the same color as said third primary color.

13. The method of claim 6 wherein the secondary color code is applied to the findings of the diseases according to the following rule:
    a fourth secondary color is assigned to second and third primary color findings if each of these findings is, by itself, very specific, though not diagnostic for its associated disease.

14. The method of claim 13 wherein said fourth secondary color is the same color as said fourth primary color.

15. The method of claim 6 wherein the secondary color code is applied to the findings of the diseases according to the following rule:
    a fourth secondary color is assigned to a fourth primary color finding if said finding is alone very specific, though not diagnostic for its associated disease.

16. The method of claim 15 wherein said fourth secondary color is the same color as said fourth primary color.

17. The method of claim 6 wherein the secondary color code is applied to the findings of the diseases according to the following rule:
    a fifth secondary color is assigned to second, third, and fourth primary color findings if each of these findings is often the only finding present with its associated disease.

18. The method of claim 6 wherein the secondary color code is applied to the findings of the diseases according to the following rule:
    a sixth secondary color is assigned to a third primary color finding if the finding is consistent with its associated disease but occurs much more frequently with other diseases.

19. The method of claim 6 wherein the secondary color code is applied to the findings of the diseases according to the following rule:
    more than one secondary color may be assigned to a primary color finding.

20. The method of claim 6 wherein the secondary color code is applied to the findings of the diseases according to the following rule:
    red is assigned as a secondary color to a first or fourth primary color finding if the finding should be used with caution in ruling in or ruling out associated disease.

21. The method of claim 1 further comprising the steps of: entering into said processing means data indicating the presence, absence or undetermined presence or absence of findings displayed in step (b); and displaying on a color display coupled to said processing means, in response to entered data, the names of diseases with which said findings are associated, said diseases assigned to a category wherein each category is formulated according to the likelihood of the disease being present in the patient.

22. The method of claim 21 wherein said categories are formulated according to the following rules:
(i) a disease is assigned to a category of eliminated diseases when associated first color findings are present, or when associated findings with the first color as a secondary color are absent;
(ii) a disease is assigned to a category of likely possibilities or diseases which must be assumed to be present until proven otherwise when any of the following are present:
   (a) all associated fourth color findings are present,
   (b) any associated finding with the fourth color as a secondary color is present,
   (c) three or more findings other than first color findings are present and no second color findings are absent,
   (d) four or more findings are present, and not more than one second color finding is absent, other than second color findings having the first secondary color associated therewith,
   (e) five or more findings are present, and not more than two second color findings are absent,
   (f) one or more fifth color findings are present,
   (g) two or more findings are present for a life or organ threatening emergency;
(iii) a disease is assigned to a category of unlikely possibilities when more than two second color findings are absent, other than second color findings having a first secondary color associated therewith; or if two or more findings are absent which have a second secondary color associated therewith.
(iv) all other diseases are assigned to a category of other possibilities 23. The method of claim 21 further comprising the step of:
displaying on a color display coupled to said processing means, in response to entered data, at least one color-coded symbol corresponding to at least one finding of a displayed disease that has not been determined to be absent or present.

24. The method of claim 21 further comprising the step of:
displaying on a color display coupled to said processing means, in response to entered data, at least one color-coded symbol corresponding to at least one finding of a displayed disease that has been determined to be absent or present.

25. An interactive computerized apparatus for presenting medical information for diagnosis and study of disease, comprising
processing means for processing data indicative of disease findings, including assigning color codes to the disease findings and categorizing the disease findings according to a set of rules;
a database containing data indicative of diseases and findings;
input means for entering data indicative of at least one of a disease or a finding to the processing means; and
output means for providing a color display of diseases and findings,
the findings being color coded and categorized on said display according to the significance of the presence or absence of each finding in ruling in or ruling out the possibility of the disease being present.

26. The apparatus of claim 25 wherein the displayed diseases are color-coded according to the following rule:
a first color is assigned to diseases that are life-threatening or organ-threatening emergencies.

27. A method of presenting medical information for diagnosis and study of disease, comprising the following steps:
(a) entering into the processing means data indicative of at least one finding or one disease;
(b) displaying on a color display coupled to the processing means, in response to entered data,
the name of at least one disease;
at least one color-coded indicator symbol, wherein said indicator symbol is color-coded according to the following rules: a first indicator symbol color indicates that the disease is a life threatening or organ threatening emergency; and a second indicator symbol color indicates that the disease is not life threatening; and
at least one color-coded indicator symbol representing at least one finding of said disease.

28. The method of claim 27 wherein said color-coded indicator symbol representing at least one finding of said disease is color coded according to the following rules:
(i) a first color indicates findings never present with a given disease;
(ii) the second primary color is assigned to findings that are at least almost always present with a given disease;
(iii) the third primary color is assigned to findings, other than second primary color findings, which are generally specific for, but not diagnostic for, a given disease:
(iv) the fourth primary color is assigned to findings that are diagnostic for a given disease.

29. The method of claim 27 wherein said first indicator symbol color is red.

30. The method of claim 27 wherein said second indicator symbol color is white.

31. The method of claim 27 further comprising the step of displaying on a color display coupled to the processing means, in response to entered data, the color-coded findings of each disease.

* * * * *